United States Patent
Garda et al.

(10) Patent No.: US 9,471,750 B2
(45) Date of Patent: Oct. 18, 2016

(54) SYSTEMS, METHODS AND COMPUTER PROGRAM PRODUCT FOR STREAMLINED MEDICATION DISPENSING

(75) Inventors: Laurie Garda, Oakmont, PA (US); Wendy Armstrong, Pittsburgh, PA (US); Jyotsna Rao, Pittsburgh, PA (US); Amy Blew, Cranberry Township, PA (US); Ryan Thomas, Wexford, PA (US); James Kolodziej, Aliquippa, PA (US); Patrick J. Braun, Pittsburgh, PA (US); Benjamin H. Tylenda, Venetia, PA (US); Shawn T. Greyshock, Tarentum, PA (US)

(73) Assignee: Aesynt Incorporated, Cranberry, PA (US)

( * ) Notice: Subject to any disclaimer, the term of this patent is extended or adjusted under 35 U.S.C. 154(b) by 455 days.

(21) Appl. No.: 13/243,626

(22) Filed: Sep. 23, 2011

(65) Prior Publication Data

US 2013/0079924 A1    Mar. 28, 2013

(51) Int. Cl.
G06F 17/00 (2006.01)
G06F 19/00 (2011.01)

(52) U.S. Cl.
CPC ....... *G06F 19/3406* (2013.01); *G06F 19/3462* (2013.01)

(58) Field of Classification Search
CPC .................................................. G06F 19/3462
USPC ................................................. 700/236–237
See application file for complete search history.

(56) References Cited

U.S. PATENT DOCUMENTS

| | | |
|---|---|---|
| 4,717,042 A | 1/1988 | McLaughlin |
| 4,785,969 A | 11/1988 | McLaughlin |
| 4,847,764 A | 7/1989 | Halvorson |
| 5,014,875 A | 5/1991 | McLaughlin et al. |
| 5,190,185 A | 3/1993 | Blechl |
| 5,314,243 A | 5/1994 | McDonald et al. |
| 5,346,297 A | 9/1994 | Colson, Jr. et al. |
| 5,377,864 A | 1/1995 | Blechl et al. |
| 5,405,048 A | 4/1995 | Rogers et al. |
| 5,431,299 A | 7/1995 | Brewer et al. |
| 5,460,294 A | 10/1995 | Williams |
| 5,468,110 A | 11/1995 | McDonald et al. |
| 5,480,062 A | 1/1996 | Rogers et al. |
| 5,520,450 A | 5/1996 | Colson, Jr. et al. |
| 5,564,803 A | 10/1996 | McDonald et al. |
| 5,593,267 A | 1/1997 | McDonald et al. |
| 5,661,978 A | 9/1997 | Holmes et al. |
| D384,578 S | 10/1997 | Wangu et al. |
| 5,713,485 A | 2/1998 | Liff et al. |

(Continued)

OTHER PUBLICATIONS

"Anywhere RN Remote Medication Management," Omnicell.com, Medication Dispensing, Overview, 2 pages, (2010). [Retrieved from the Internet Apr. 26, 2012: <URL: http://omnicorpprod.omnicell.com/Solutions/Medication-Dispensing/Pages/AnywhereRN.aspx>].

(Continued)

*Primary Examiner* — Michael K Collins
(74) *Attorney, Agent, or Firm* — Alston & Bird LLP

(57) ABSTRACT

Methods, apparatuses and computer program products are provided for facilitating the expedited dispensing of medications from an automated medication storage device. In this regard, a method may cooperate with the first device to facilitate the presentation of various displays that include features to reduce number of user interactions to dispense medications safely and effectively.

24 Claims, 14 Drawing Sheets

(56) References Cited

U.S. PATENT DOCUMENTS

| | | | | |
|---|---|---|---|---|
| 5,716,114 | A | 2/1998 | Holmes et al. | |
| 5,745,366 | A | 4/1998 | Higham et al. | |
| 5,761,877 | A | 6/1998 | Quandt | |
| 5,797,515 | A | 8/1998 | Liff et al. | |
| 5,805,456 | A | 9/1998 | Higham et al. | |
| 5,842,976 | A | 12/1998 | Williamson | |
| 5,878,885 | A | 3/1999 | Wangu et al. | |
| 5,880,443 | A | 3/1999 | McDonald et al. | |
| 5,883,806 | A | 3/1999 | Meador et al. | |
| 5,893,697 | A | 4/1999 | Zini et al. | |
| 5,905,653 | A | 5/1999 | Higham et al. | |
| 5,912,818 | A * | 6/1999 | McGrady | G06M 7/04 700/214 |
| 5,927,540 | A | 7/1999 | Godlewski | |
| 5,940,306 | A | 8/1999 | Gardner et al. | |
| 5,971,593 | A | 10/1999 | McGrady | |
| 6,003,006 | A | 12/1999 | Colella et al. | |
| 6,011,999 | A | 1/2000 | Holmes | |
| 6,021,392 | A | 2/2000 | Lester et al. | |
| 6,039,467 | A | 3/2000 | Holmes | |
| 6,065,819 | A | 5/2000 | Holmes et al. | |
| 6,068,156 | A | 5/2000 | Liff et al. | |
| 6,109,774 | A | 8/2000 | Holmes et al. | |
| 6,112,502 | A | 9/2000 | Frederick et al. | |
| 6,116,461 | A | 9/2000 | Broadfield et al. | |
| 6,151,536 | A * | 11/2000 | Arnold | G07F 17/0092 700/236 |
| 6,170,230 | B1 | 1/2001 | Chudy et al. | |
| 6,170,929 | B1 * | 1/2001 | Wilson et al. | 312/268 |
| 6,176,392 | B1 | 1/2001 | William et al. | |
| 6,189,727 | B1 | 2/2001 | Shoenfeld | |
| 6,223,934 | B1 | 5/2001 | Shoenfeld | |
| 6,256,967 | B1 | 7/2001 | Hebron et al. | |
| 6,283,322 | B1 | 9/2001 | Liff et al. | |
| 6,289,656 | B1 | 9/2001 | Wangu et al. | |
| 6,338,007 | B1 | 1/2002 | Broadfield et al. | |
| 6,339,732 | B1 | 1/2002 | Phoon et al. | |
| 6,361,263 | B1 | 3/2002 | Dewey et al. | |
| 6,370,841 | B1 | 4/2002 | Chudy et al. | |
| 6,449,927 | B2 | 9/2002 | Hebron et al. | |
| 6,471,089 | B2 | 10/2002 | Liff et al. | |
| 6,497,342 | B2 | 12/2002 | Zhang et al. | |
| 6,499,270 | B2 | 12/2002 | Peroni et al. | |
| 6,532,399 | B2 | 3/2003 | Mase | |
| 6,564,121 | B1 | 5/2003 | Wallace et al. | |
| 6,581,798 | B2 | 6/2003 | Liff et al. | |
| 6,609,047 | B1 | 8/2003 | Lipps | |
| 6,611,733 | B1 | 8/2003 | De La Huerga | |
| 6,625,952 | B1 | 9/2003 | Chudy et al. | |
| 6,636,780 | B1 * | 10/2003 | Haitin et al. | 700/236 |
| 6,640,159 | B2 | 10/2003 | Holmes et al. | |
| 6,650,964 | B2 | 11/2003 | Spano, Jr. et al. | |
| 6,671,579 | B2 * | 12/2003 | Spano et al. | 700/236 |
| 6,681,149 | B2 | 1/2004 | William et al. | |
| 6,742,671 | B2 | 6/2004 | Hebron et al. | |
| 6,755,931 | B2 | 6/2004 | Vollm et al. | |
| 6,760,643 | B2 | 7/2004 | Lipps | |
| 6,776,304 | B2 | 8/2004 | Liff et al. | |
| 6,785,589 | B2 | 8/2004 | Eggenberger et al. | |
| 6,790,198 | B1 | 9/2004 | White et al. | |
| 6,814,254 | B2 | 11/2004 | Liff et al. | |
| 6,814,255 | B2 | 11/2004 | Liff et al. | |
| 6,847,861 | B2 | 1/2005 | Lunak et al. | |
| 6,874,684 | B1 | 4/2005 | Denenberg et al. | |
| 6,892,780 | B2 | 5/2005 | Vollm et al. | |
| 6,895,304 | B2 | 5/2005 | Spano, Jr. et al. | |
| 6,975,922 | B2 | 12/2005 | Duncan et al. | |
| 6,985,797 | B2 | 1/2006 | Spano, Jr. et al. | |
| 6,996,455 | B2 | 2/2006 | Eggenberger et al. | |
| 7,010,389 | B2 | 3/2006 | Lunak et al. | |
| 7,014,063 | B2 | 3/2006 | Shows et al. | |
| 7,016,766 | B2 | 3/2006 | William et al. | |
| 7,040,504 | B2 | 5/2006 | Broadfield et al. | |
| 7,052,097 | B2 | 5/2006 | Meek, Jr. et al. | |
| 7,072,737 | B2 | 7/2006 | Lunak et al. | |
| 7,072,855 | B1 | 7/2006 | Godlewski et al. | |
| 7,077,286 | B2 | 7/2006 | Shows et al. | |
| 7,085,621 | B2 | 8/2006 | Spano, Jr. et al. | |
| 7,092,796 | B2 | 8/2006 | Vanderveen | |
| 7,093,755 | B2 | 8/2006 | Jordan et al. | |
| 7,100,792 | B2 | 9/2006 | Hunter et al. | |
| 7,103,419 | B2 | 9/2006 | Engleson et al. | |
| 7,111,780 | B2 | 9/2006 | Broussard et al. | |
| 7,139,639 | B2 | 11/2006 | Broussard et al. | |
| 7,150,724 | B2 | 12/2006 | Morris et al. | |
| 7,155,306 | B2 * | 12/2006 | Haitin et al. | 700/242 |
| 7,171,277 | B2 | 1/2007 | Engleson et al. | |
| 7,203,571 | B2 * | 4/2007 | Kirsch | G07F 17/0092 700/236 |
| 7,218,231 | B2 | 5/2007 | Higham | |
| 7,228,198 | B2 | 6/2007 | Vollm et al. | |
| 7,249,688 | B2 | 7/2007 | Hunter et al. | |
| 7,263,411 | B2 * | 8/2007 | Shows | G06F 19/3462 221/2 |
| 7,348,884 | B2 | 3/2008 | Higham | |
| 7,417,729 | B2 | 8/2008 | Greenwald | |
| 7,419,133 | B2 | 9/2008 | Clarke et al. | |
| 7,426,425 | B2 | 9/2008 | Meek, Jr. et al. | |
| 7,554,449 | B2 | 6/2009 | Higham | |
| 7,571,024 | B2 | 8/2009 | Duncan et al. | |
| 7,588,167 | B2 | 9/2009 | Hunter et al. | |
| 7,689,316 | B1 * | 3/2010 | Frederick | G06F 19/327 700/231 |
| 7,885,725 | B2 * | 2/2011 | Dunn | 700/237 |
| 8,170,714 | B2 * | 5/2012 | Spano et al. | 700/237 |
| 8,554,365 | B2 * | 10/2013 | Thomas | G06F 19/3462 700/236 |
| 2001/0032035 | A1 * | 10/2001 | Holmes | A47B 88/20 700/231 |
| 2003/0120384 | A1 * | 6/2003 | Haitin et al. | 700/242 |
| 2007/0088461 | A1 * | 4/2007 | Haitin et al. | 700/241 |
| 2007/0156282 | A1 * | 7/2007 | Dunn | 700/244 |
| 2009/0037020 | A1 * | 2/2009 | Brown | 700/240 |
| 2009/0210247 | A1 * | 8/2009 | Chudy | G06F 19/3462 705/2 |
| 2010/0145506 | A1 * | 6/2010 | Waugh et al. | 700/231 |
| 2010/0198401 | A1 * | 8/2010 | Waugh et al. | 700/237 |

OTHER PUBLICATIONS

"OmniRx G4 Medication Dispensing Cabinets," Omnicell.com, Automated Dispensing Cabinets, Software, 2 pages, (2010). [Retrieved from the Internet Apr. 26, 2012: <URL: http://omnicorp-prod.omnicell.com/Solutions/Medication-Dispensing/Automated-Dispensing-Cabinets/Pages/OmniRX.aspx>].

* cited by examiner

SYSTEMS, METHODS AND COMPUTER PROGRAM PRODUCT FOR STREAMLINED MEDICATION DISPENSING

TECHNOLOGICAL FIELD

Embodiments of the present invention relate generally to drawer assemblies and associated methods and, more particularly, to drawer assemblies and associated methods that aid in facilitating the dispensing of medication.

BACKGROUND

Medication dispensing cabinets have been developed to store and controllably dispense a variety of medications. A medication dispensing cabinet may include a cabinet body with one or more drawers that are slideably disposed within the cabinet body. The drawers store the various medications. While some of the drawers may be unlatched and freely openable, other drawers may be locked in order to more closely control access to the medications stored in the locked drawers.

Some medication dispensing cabinets are automated and, as such, include or are otherwise associated with a computer that controls access to the medication stored within the cabinet. The computer may allow access to only authorized users, such as medical providers who work in the unit in which the medication dispensing cabinet is located. Once authorized by the computer, a medical provider may identify a particular medication to be dispensed, such as by reference to the medications prescribed to a respective patient to whom the medical provider is attending. The computer may then unlock the respective drawer in which the particular medication is stored so as to provide access to the medication.

The amount of time it takes for the medical provider to interact with the computer and access the respective drawer can vary based on the type of medication dispensing cabinets and their computer control systems. While medication dispensing cabinets are an important tool in loss prevention of narcotics as well as in providing the proper medication to each patient, any time spent interacting with the medication dispensing cabinets is time that the medical providers cannot be with their patients. Moreover, lines of medical providers sometimes form at the medication dispensing cabinets further reducing medical providers' time with patients.

Furthermore, with the industry's current trend to move more medications to the nursing floor (from centralized pharmacies), the average number of medications being removed from a medication dispensing cabinet for a patient on a typical morning has increased from two (typically "as needed" pain medications) to twelve (typically all oral and/or injectable medications prescribed for a patient). As a result, there is an increasing risk that medical providers may miss medications when scanning through the patient orders to select the medications to be dispensed.

Accordingly, there is a need for an improved system and method for dispensing medication that allows healthcare professionals to dispense medication for the patients under their care in a more rapid, efficient, and accurate manner.

BRIEF SUMMARY

Methods, apparatuses and computer program products are provided according to embodiments of the present invention for dispensing medications. In some embodiments, the medications may be dispensed from one or more drawers. A processor can also be provided that is configured to generate a first display on a display component, the first display comprising a patient list identifying one or more patients. In response to determining there was a first user input to select a selected patient included in the patient list, the processor can be configured to generate a medication list of one or more medications associated with the selected patient, and the medication list can be presented on the display component. In response to determining there was one or more additional user inputs indicating a desire to modify the medication list, the processor can be configured to generate a modified list including selected medications and selected quantities of the selected medications to be dispensed for the selected patient. When it is time to dispense the medications, the processor can be configured to determine a targeted drawer that stores at least one of the selected medications, and generate an unlock command that causes the targeted drawer to unlock.

In some embodiments, the processor is further configured to be directed by the one or more additional user inputs to change the selected quantity associated with at least one of the selected medications. The storage device's processor may also be configured to be directed by the one or more additional user inputs to deselect at least one of the selected medications to prevent dispensing.

As yet another example, the storage device's processor can be further configured to be directed by the one or more additional user inputs to determine an order to dispense the selected medications.

The storage device can also comprise at least one sensor that monitors the medication that is dispensed.

In some embodiments, the storage device can be further configured to generate an updated list as the selected medications are dispensed by removing dispensed medications from the modified list as the dispensed medications are removed from the selected drawer. A memory component can also be included in the storage device and, in response to determining that dispensing has been interrupted, be used to save the updated list of medications.

As another example, the storage device's processor can be further configured to generate the medication list based at least partially upon the time of day that the first user input is received and/or the particular user of the medication storage device.

Some embodiments may also be configured to present the first display when the one or more drawers are in the closed position and/or present the medication list of the one or more medications associated with the selected patient by presenting a quantity associated with each of the one or more medications in the medication list.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the invention in any way. It will be appreciated that the scope of the invention encompasses many potential embodiments, some of which will be further described below, in addition to those here summarized.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIGS. 8-15B are example screen displays that may be presented by some embodiments of the present invention discussed herein.

DETAILED DESCRIPTION

Figure 1:
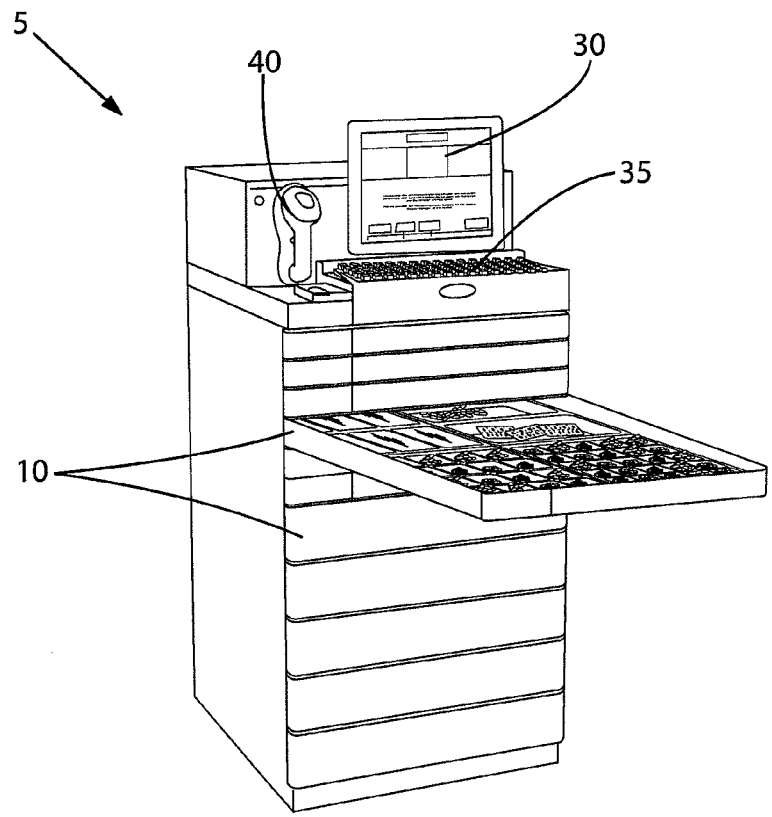
FIG. 1 illustrates an automated storage device in accordance with some example embodiments discussed herein.

Embodiments of the present inventions now will be described more fully hereinafter with reference to the accompanying drawings, in which some, but not all embodiments of the inventions are shown. Indeed, embodiments of these inventions may be embodied in many different forms and should not be construed as limited to the embodiments set forth herein; rather, these embodiments are provided so that this disclosure will satisfy applicable legal requirements. Like reference numerals refer to like elements throughout.

The storage devices, systems, and methods of embodiments of the present invention may be used by healthcare facilities, such as hospitals, physicians' offices, healthcare clinics, and any other facility that manages and/or dispenses drugs for patient use. The storage devices, systems, and methods described herein provide a more streamlined and efficient way for healthcare professionals to interface with an automated storage device, such as an automated dispensing cabinet (ADC), to dispense medications. Although nurses are often tasked with accessing medication stored in an automated storage device, and the example of a nurse is used in the description that follows, it is understood that the described embodiments apply to any user who is interfacing with the automated storage device, including physicians, pharmacists, nurses, laboratory personnel, respiratory therapists, and others. Furthermore, although the example of a user interfacing with an automated storage device for the purpose of dispensing medications to administer to patients is predominantly described below, one skilled in the art in light of this disclosure would recognize that the embodiments are also applicable to users interfacing with the automated storage device for the purpose of restocking medication, taking inventory, and performing other tasks that may require access to the medication stored in the automated storage device. In addition, the phrase "storage device" is intended to include any type of automated storage device, including an automated dispensing cabinet (ADC), unit-based cabinet (UBC), automated dispensing device (ADD), automated distribution cabinet, medication dispensing cabinet, and automated dispensing machine (ADM), among others. And the use of "dispensing" herein refers to any type of removal of any object from a storage device for any reason, and is not limited to the dispensing of medication by a nurse for administration to a patient.

Turning now to FIG. 1, a storage device 5 is shown. For example, some embodiments of the storage device 5 can be similar to and/or include components that are currently included in the cabinets sold and marketed as McKesson's AcuDose-RX™ cabinets. The storage device 5 may be configured to store a number of different types and quantities of medications. In this regard, the storage device 5 may include (e.g., define) a plurality of drawers 10. Different types of storage devices 5 may include different sizes and styles of drawers 10, depending on, for example, the types of medications to be stored in the drawers, the quantities required (which may be dictated by the size or type of the facility or other area serviced by the automated storage device), and user preferences. For example, some drawers 10 may be deep, whereas others may be shallower. In addition, access to the drawers 10 may be restricted to certain authorized users and may further be accessible only when medication stored in the particular drawer is to be dispensed, as described in greater detail below. Accordingly, each drawer 10 may be in a locked state until an authorized user interfaces with the storage device 5 to select for dispensing a particular medication stored within a particular drawer, at which point the storage device may unlock and/or open the drawer containing the selected medication to allow the user's access.

The drawers 10 may hold more than just medications, in some cases. For example, certain medical accessories or supplies may also be stored in the automated storage device 5, such as applicators, syringes, keys, prescription pads, cameras, etc., which may also be dispensed by the nurse during an interaction with the storage device. Accordingly, although the examples provided below refer to the dispensing of medications, the dispensing and transport of any item stored in the storage device 5, such as medical accessories, is contemplated herein.

In some embodiments, the storage device 5 further includes a display device 30. The display device 30 may be a monitor, as depicted, and may be configured to present various items of medication dispensing information related to a selected patient for the user to view, as described below. For example, the user may be able to view medication dispensing information regarding the patients assigned to a particular nurse's shift or other patients to whose records the nurse has access, as well as medication dispensing information relating to the medications stored in the storage device 5 and/or other storage devices in communication with the storage device 5.

For example, using the display device 30, the user may be able to view a list of patients under the user's care; view patient details (e.g., patient's name, date of birth, medical condition, allergies, date of admittance, date of expected discharge, etc.); view a list of prescribed medications for a particular patient; view medication details (such as potential interactions, medication properties, and dosage information); and/or view order details (such as the name of a medication, required dosage, quantity to be dispensed, location of the medication in the storage device (drawer and pocket), etc.). Examples of methods for presenting this and/or other information are discussed below in connection with FIGS. 6A-7.

Similarly, the display device 30 may also be configured to function as user input device. For example, the display device 30 may include one or more touch-sensitive components and associated hardware, software and/or firmware. Additionally or alternatively, one or more dedicated user input devices, such as the user input device 35 and/or user input device 40 shown in FIG. 1, which can be mounted to or otherwise associated with the storage device. The various user input devices that can be used with or included in the storage device 5, e.g., the display device 30, user input device 35 and user input device 40, are sometimes referred to herein as "user input devices." The components that facilitate the generation of electrical signals associated with a user's interaction with the user input device are sometimes referred to herein as "user input components." For example, the display device 30 may function as both a user input and output device. Its touch-sensitive components may be considered user input components and its display components may be considered user output components. Other examples of user output components include lights, audio speakers, haptic feedback components, and/or any other device that may generate stimuli detectable by a user.

User input devices may be configured to receive input from the user regarding at least one dispensing transaction. In this regard, the term "dispensing transaction" is used herein to describe the interfacing between the user and the storage device to dispense one or more medications to be administered to a single patient. Thus, each dispensing transaction is associated with a particular selected patient. Furthermore, each user may have multiple dispensing transactions with the storage device in a single interaction with the storage device. In this regard, the window between the time a user logs into the system (e.g., provides identification credentials indicating that the user is authorized to have access to the medications stored within the storage device) to the time the user logs out of the system (which may require, e.g., a log-out event by the same user or resulting from an expiration of a predetermined period of time, or a log-in event by a different user for access to the storage device) may define the interaction, whereas the time it takes for the user to dispense medications relating to a particular patient may define the dispensing transaction. Thus, a user may have multiple dispensing transactions for multiple patients in a single user interaction with the storage device.

With continued reference to FIG. 1, one or more user input devices may be configured to receive user input regarding a particular dispensing transaction. For example, a user input device may receive input in the form of identification credentials authorizing the user to access the storage device 5 and/or a particular drawer 10 of the storage device 5; a selection of a patient for whom medication is to be dispensed; a request for information regarding a particular medication stored in one of the drawers or a particular patient to whose records the user has access; a selection of a particular medication to be viewed or dispensed; and so on. As another example, the user input device(s) may be configured to receive user input regarding an inventory of a particular drawer 10 or multiple drawers, such as a count of the medications remaining in a particular drawer or pocket of the drawer after a medication has been dispensed. Furthermore, in some cases, the storage device 5 may be configured to communicate with other storage devices in other parts of the healthcare facility, such that the user may be able to enter input requesting information regarding the contents of the other storage devices. Additional examples of methods that include the storage device receiving and responding to user inputs are discussed below in connection with FIGS. 6A-7.

Different types of storage devices 5 may include different sizes and styles of drawers 10, depending on the types of medications to be stored in the drawers, the quantities required (which may be dictated by the size of the facility), and user preferences. For example, as shown in FIG. 1, some drawers 10 may be deep, whereas others may be shallower. In addition, access to the drawers 10 may be restricted to certain authorized users and may further be accessible only when medication stored in the particular drawer is to be dispensed, as described in greater detail below. Additionally or alternatively, each pocket may also be locked with a lid (discussed below) that the storage device 5 is configured to unlock only when medication stored in the particular pocket is to be dispensed. Accordingly, each drawer 10 and/or pocket may be in a locked state until an authorized user interfaces with the storage device 5 to dispense a particular medication stored within a particular drawer and/or pocket, at which point the storage device may unlock and/or open the drawer and/or pocket containing the selected medication to allow the user's access. In some cases, the storage device 5 may unlock all of its drawers 10, all its pockets or all its pockets within a given drawer upon determining a particular user's authorization level to the storage device, regardless of the specific location(s) of the particular medication requested.

Figure 1A:
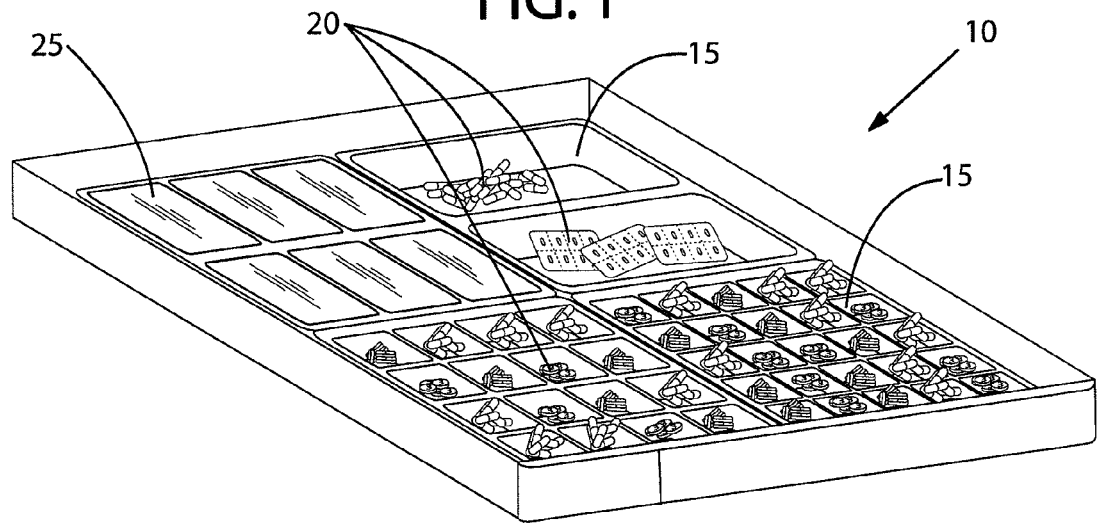
FIG. 1A illustrates an automated storage device in accordance with some example embodiments discussed herein.

In this regard, as shown in FIG. 1A, each drawer 10 may define a plurality of pockets 15 that are each configured to store at least one medication 20 or type of medication. Thus, depending on the size, form (e.g., liquid, pill, capsule, etc.), packaging (e.g., cartridge strip, bottle, etc.), and/or special requirements for the medication (e.g., restricted access, such as a narcotic; medication requiring refrigeration; etc.), the configuration of the pocket 15 (e.g., size and shape) may also be different from one drawer 10 to the next or within the same drawer. For example, in the depicted embodiment of FIG. 1A, the pockets 15 defined by the open drawer 10 include four sizes of pockets to accommodate different types of medication. Furthermore, some pockets 15 may include lids 25 to keep the contents of the pocket in place. The lids 25 may be clear, to allow the user to view the contents of the pocket 15 with the lid closed, and others may be opaque, obscuring the view of the contents. In still other cases, the lids 25 may be locked (not shown) until access by an authorized user to the contents of the locked lid is granted, at which time the lid may be unlocked and/or opened to allow retrieval of the medication 20 stored therein.

Figure 2:
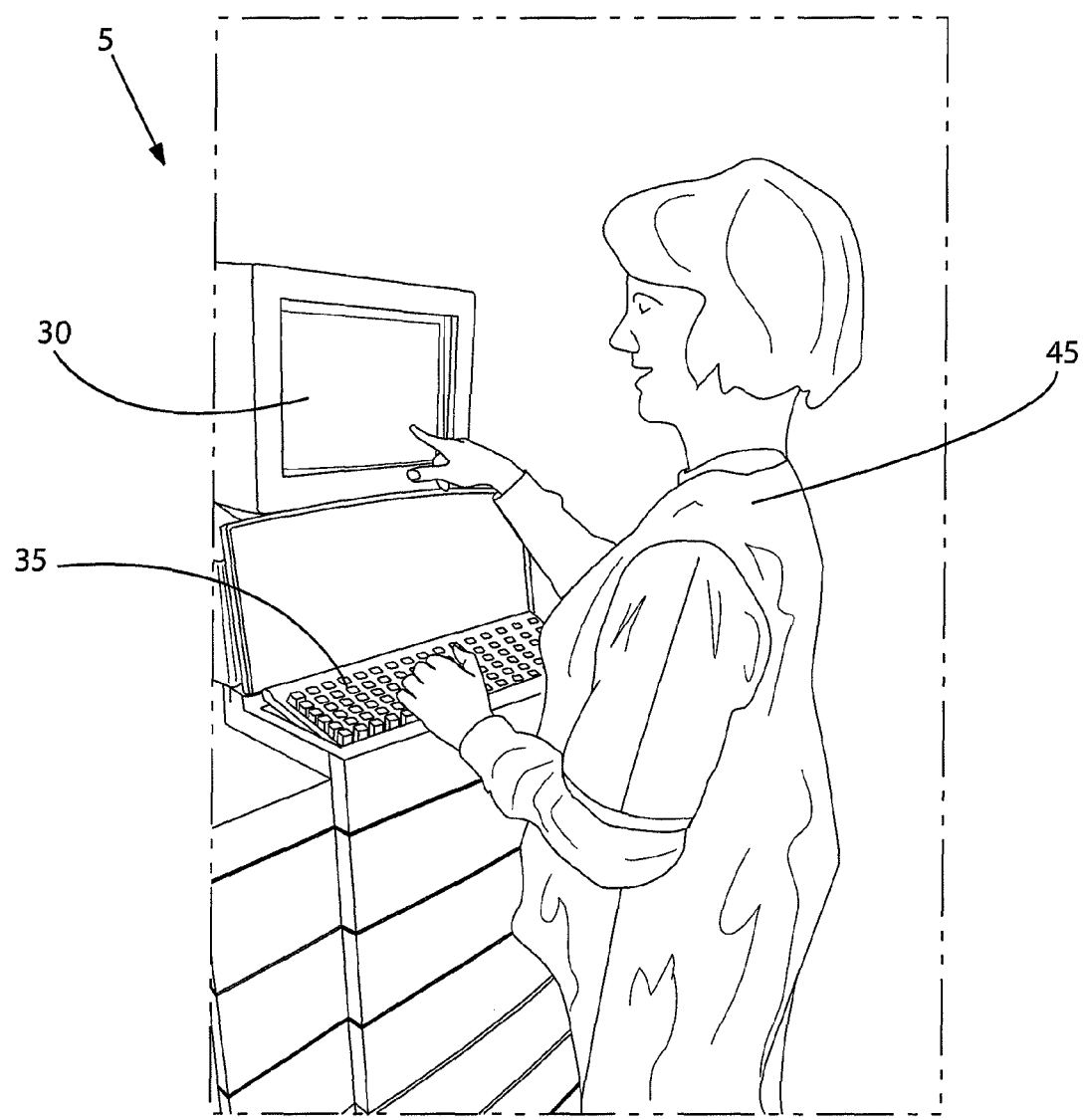
FIGS. 2 and 3 illustrate a user interacting with automated storage device in accordance with some example embodiments discussed herein.

As noted above, more than one user input device may be included in and/or configured to interface with the storage device 5. For example, as shown in FIGS. 1 and 2, the storage device 5 includes the touch-sensitive display 30, the user input device 35 in the form of a keyboard and the additional user input device 40 in the form of a barcode reader. The barcode reader may be configured to scan barcodes off medication packaging, and/or the barcode reader may be configured to read a user's identification credentials (e.g., badge, bracelet, key, etc.) to ascertain whether the user has access to a particular storage device and/or access to a particular medication, as well as to track and trend access to the storage device, such as for taking inventory and generating reports regarding users. Other examples of user input devices may include a mouse, microphone, biometric reader, and/or a camera, among others.

The storage device 5 may also include one or more other components and/or may provide one or more other functions not specifically discussed herein. For example, the storage device 5 may include a container dispensing device mounted to or otherwise supported by the storage device. The container dispensing device may be configured to store and dispense containers, and each container may be configured to receive one or more dispensed medications for administering to a single selected patient. Thus, each container may be configured to allow the secure transport of the dispensed medications received therein between the storage device 5 and the selected patient's bedside.

As shown in FIG. 2, the location of the display device 30 and the various other user input devices of the storage device 5 allows the user 45, such as the nurse, to have comfortable access to the cabinet-level display device and the cabinet-level user input device when standing in front of the storage device, as shown, or an associated storage device nearby. In this way, the user 45 may be able to view and manipulate various types of medication information upon first approaching the storage device 5, in the standing position (e.g., before accessing any of the drawers 10 to dispense medication).

Once the user has initially interfaced with the display device 30 and/or the user input device(s) 35, 40, for example, to log-in, one or more sets of screens and/or methods may be implemented by the storage device 5. Examples of these methods are discussed in connection with FIGS. 6A-7 and generally include, for example, improved processes and more efficient means of enabling the user 45 to view and/or select a particular patient's list of medications, select medication(s) to be dispensed, access a locked drawer and/or lid, among other things.

Figure 3:
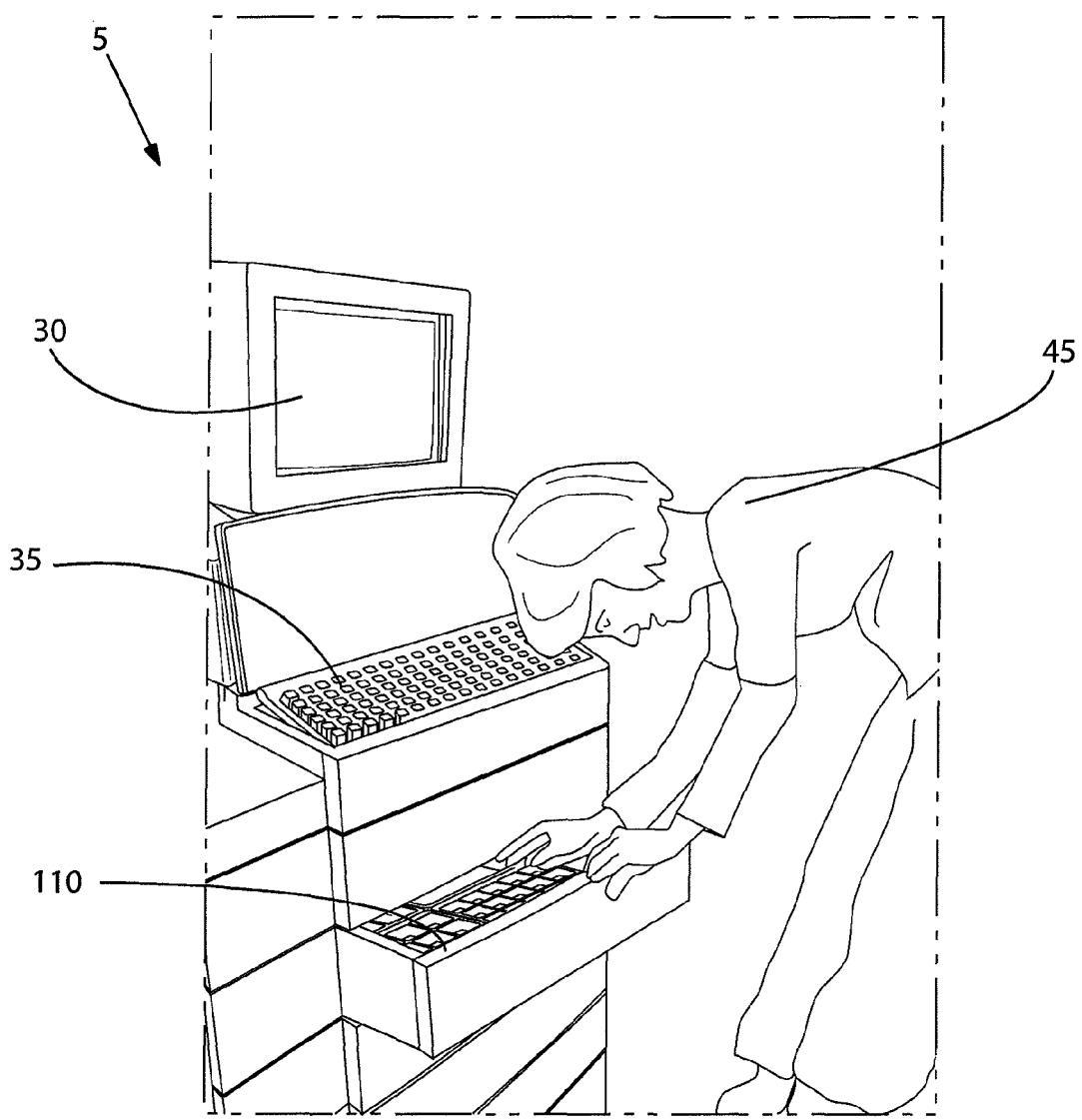

In some cases, the display device 30 and/or various other output devices may be used to direct the user 45 as to which pocket 15 should be accessed to dispense the selected medication. For example, the storage device 5 may be configured to indicate the particular pocket via a light emitting diode (LED) and/or other indicator associated with particular pocket to be accessed. In this way, the user 45 would, upon looking into the identified drawer, as shown in FIG. 3, visually determine which pocket is to be accessed.

Figure 4:
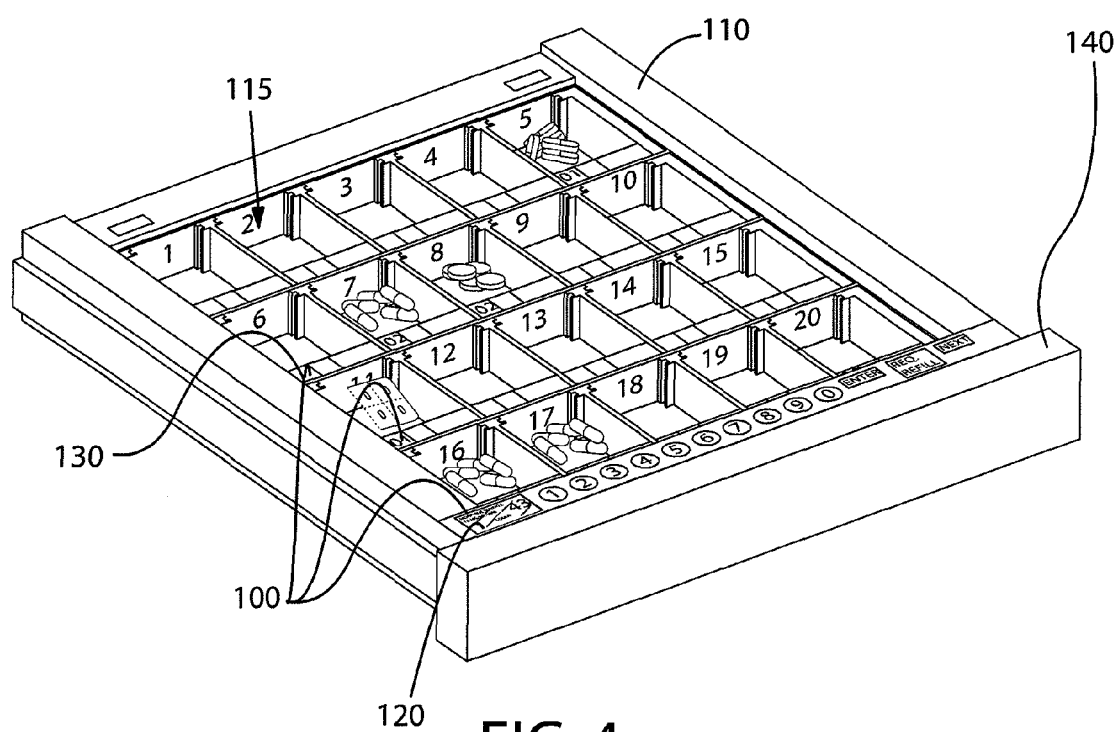
FIGS. 4, 4A and 4B illustrate various views of a drawer in accordance with some example embodiments discussed herein.
Figures 4A, 4B:
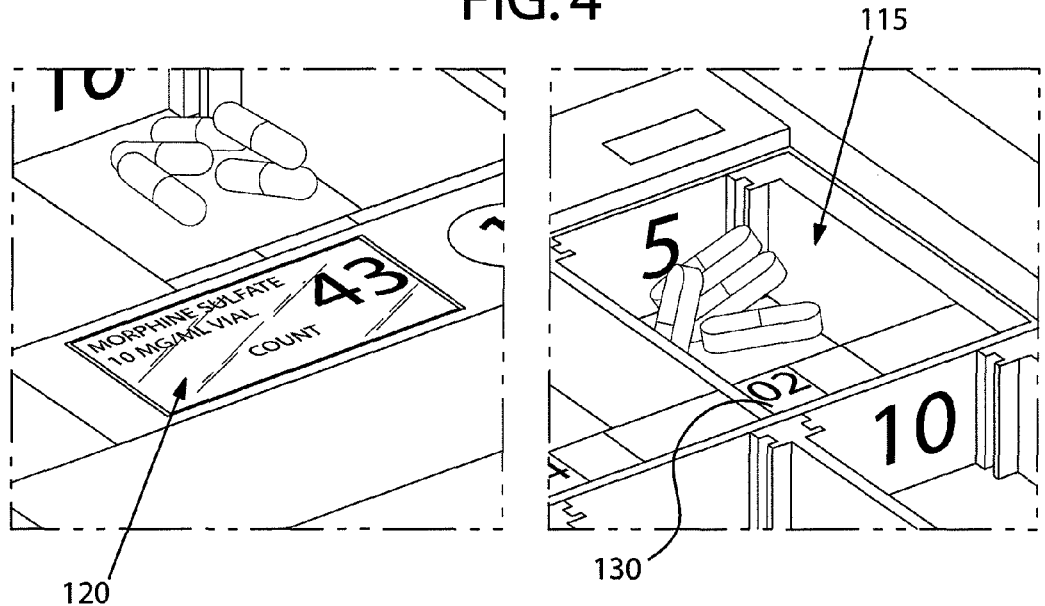

Accordingly, some embodiments of the storage device 5 may also include a plurality of drawer-level display devices 100, shown in FIGS. 4-4B. Each drawer-level display device 100 may be associated with and disposed on a particular drawer 110. Each drawer-level display device 100 may be configured to present a user with medication information for a selected medication stored in the associated drawer 110. In particular, the medication information may include at least one of a name of the selected medication (e.g., the chemical name of the medication, a common name for the medication used in the industry, a chemical compositions for the medication, and/or a code or alpha-numeric designation identifying the medication, such as a system designator for the particular medication), a quantity of the selected medication to be dispensed, a dosage of the medication to be dispensed, and/or medication inventory information. In this way, the user 45 can have direct access to information required for completing a dispensing operation at the identified (accessed) drawer and does not need to refer back to the display device 30 (for example, if the nurse had forgotten how many units were to be dispensed according to the prescription) after the drawer and/or lids are unlocked and/or opened. In other words, the information needed to complete a dispensing operation that is in progress can be found at the drawer-level, where the user's attention is already focused.

The drawer-level display devices 100 may include main drawer-level display devices 120, secondary drawer-level display devices 130, or may include both main drawer-level display devices and secondary drawer-level display devices. For example, at least some of the drawer-level display devices 100 may be main drawer-level display devices 120. Each main drawer-level display device may be disposed proximate a leading edge 140 of the respective associated drawer 110, such that upon opening the drawer, the user would quickly see the main drawer-level display device, even if the drawer is not fully open. In other cases, however, the main drawer-level display device 120 may be located elsewhere on the drawer 110, such as on a front panel or on the side of each drawer and may be visible to the user even when the drawer is closed.

Each drawer 110 may have one main drawer-level display device 120 associated with it, and thus the user may be able to view at least certain medication information relating to the medication in the particular associated drawer via the main drawer-level display device. For example, as shown in FIG. 4A, the main drawer-level display device 120 may be configured to present to the user a name of the selected medication to be dispensed, a quantity of the medication to be dispensed, a prescribed dosage, a location of the selected medication (e.g., pocket identifier), and/or an inventory of the selected medication that is stored in the identified pocket, among other things. The main drawer-level display device 120 may be an LCD (liquid crystal display) screen, for example. Moreover, the information displayed via the main drawer-level display device 120 may be configurable by the user, such that only certain information is displayed.

In other cases, at least some of the drawer-level display devices may be secondary drawer-level display devices 130, and each secondary drawer-level display device may be associated with and disposed proximate at least one of the pockets 115 defined by the associated drawer 110. For example, each pocket 115 may have a dedicated secondary drawer-level display device 130 associated with it, as shown in FIG. 4B. In other cases, however, two or more pockets may share the same secondary drawer-level display device. Each secondary drawer-level display device 130 may be configured to present to a user a quantity of the selected medication to be dispensed from the associated pocket. For example, in FIG. 4B, the selected medication is stored in Pocket 5. Accordingly, the secondary drawer-level display device 130 associated with Pocket 5 is activated and indicates that 2 units of the selected medication are to be dispensed. In other words, the display of the number "2" on the secondary drawer-level display device 130 in this case serves dual purposes—it both identifies which pocket is the identified pocket from which the selected medication is to be dispensed, and it indicates the quantity of the selected medication to be dispensed from that pocket. In this regard, the secondary drawer-level display device 130 may include one or more of an LCD, LED, or other similar display technology.

Figure 5:
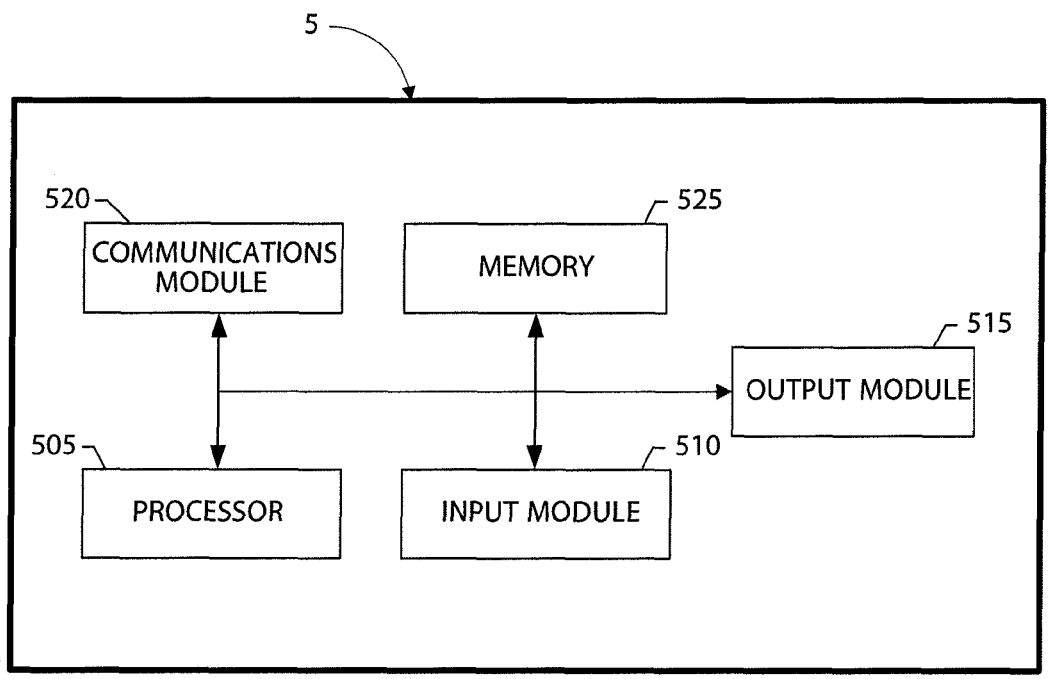
FIG. 5 is a block diagram of an apparatus that may be included in embodiments discussed herein.

Referring now to FIG. 5, the storage device 5 may include any type of circuitry to facilitate the functionality discussed herein. For example, circuitry commonly found in various computing devices and other types of machines (e.g., desktop computer, laptop computer, tablet, etc.), may be included in the storage device 5. For example, FIG. 5 shows a block diagram of example circuitry components that may be configured to store and/or execute computer-readable program code portions comprising executable instructions and/or other types of executable portions. As such, the storage device 5 may include various means for performing one or more functions in accordance with some embodiments, including those more particularly shown and described herein. It should be understood, however, that the storage device 5 may include alternative means for performing one or more like functions, without departing from the spirit and scope of embodiments discussed herein. As shown, the storage device 5 is a machine and can generally include means, such as processor 505 for performing or controlling the various functions of the storage device 5.

The processor 505 may, for example, be embodied as various means including one or more microprocessors with accompanying digital signal processor(s), processor(s) without an accompanying digital signal processor, one or more coprocessors, multi-core processors, controllers, computers, various other processing elements including integrated circuits such as, for example, an ASIC (application specific integrated circuit) or FPGA (field programmable gate array), or some combination thereof. Accordingly, although shown in FIG. 5 as a single processor, in some embodiments the processor 505 comprises a plurality of processors and/or any other type of control circuitry. The plurality of processors, for example, may be embodied on a single computing device or may be distributed across a plurality of computing devices collectively configured to function as the processor 505. The plurality of processors may be in operative communication with each other and may be collectively configured to perform one or more functionalities of the processor 505 as described herein. In an example embodiment, the processor 505 is configured to execute instructions stored in the memory 525 (discussed below) and/or that are otherwise accessible to the processor 505. These instructions, when executed by the processor 505, may cause the storage device 5 to perform one or more of the functionalities described herein. As such, whether configured by hardware, firmware/software methods, or by a combination thereof, the processor 505 may comprise an entity capable of performing operations according to embodiments of the present invention while configured accordingly. Thus, for example, when the processor 505 is embodied as an ASIC, FPGA or the like, the processor 505 may comprise specifically configured hardware for conducting one or more operations described herein. Alternatively, as another example, when the processor 505 is embodied as an executor of instructions, such as may be stored in the memory 525, the instructions may specifically configure the processor 505 to perform one or more algorithms and operations described herein.

The processor 505 may be configured to receive a signal from the input module 510, which may include specialized circuitry, one or more ports (serial, such as universal serial bus "USB" ports, and/or parallel ports), and/or any other component that facilitates the reception of signals from an input component. In some embodiments, the input module 510 can function as a user input interface and, in turn, receive data from any of a number and/or types of devices and/or users. For example, the input module 510 may be electrically coupled to the display device 30, the user input device 35 and/or the user input device 40. Although more than one input module can be included in the storage device 5, only one is shown in FIG. 5 (like the other components discussed herein) to avoid overcomplicating the drawing.

The processor 505 can also be configured to utilize the communications module 520 to communicate with one or more remote machines (e.g., via a network). The communications module 520 can include hardware, software, and/or any other means for transmitting and/or receiving data, content or any other type of information from a network or other type of device.

In some embodiments, the processor 505 is in communication with or includes memory 525, such as volatile and/or non-volatile memory that stores content, data and/or any other information. For example, the memory 525 can store information generated by, transmitted from, and/or received by, the storage device 5. Also for example, the memory 525 typically stores software applications, instructions or the like for the processor 505 to perform steps associated with operation of the storage device 5. For example, the memory 525 may be a non-transitory storage medium that stores computer program code comprising instructions or other executable portions that the processor 505 executes to perform the steps described above and below with regard to, e.g., FIGS. 6A-7.

Figure 6A:
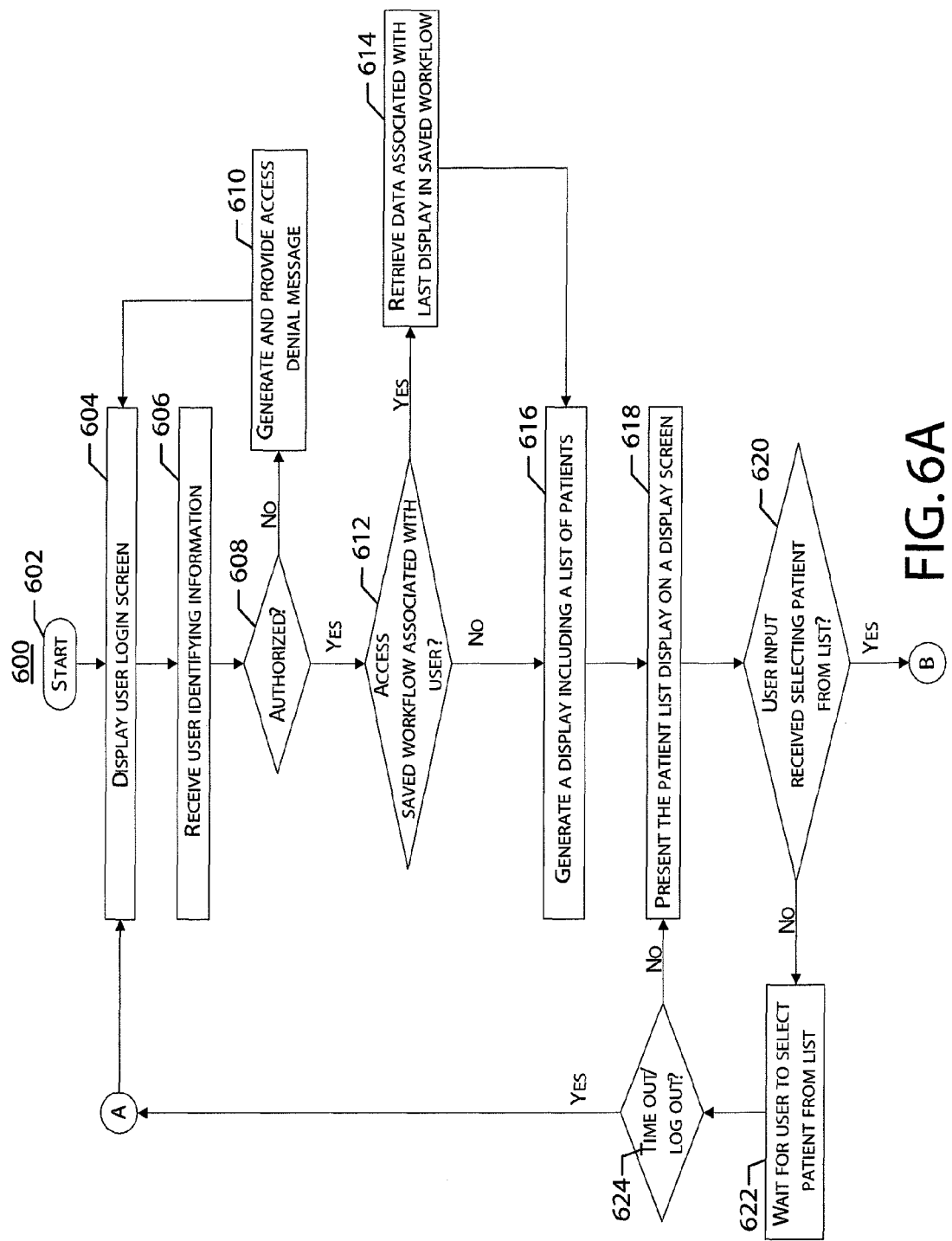
FIGS. 6A-7 are example flowcharts illustrating operations performed in accordance with some embodiments of the present invention.
Figure 6B:
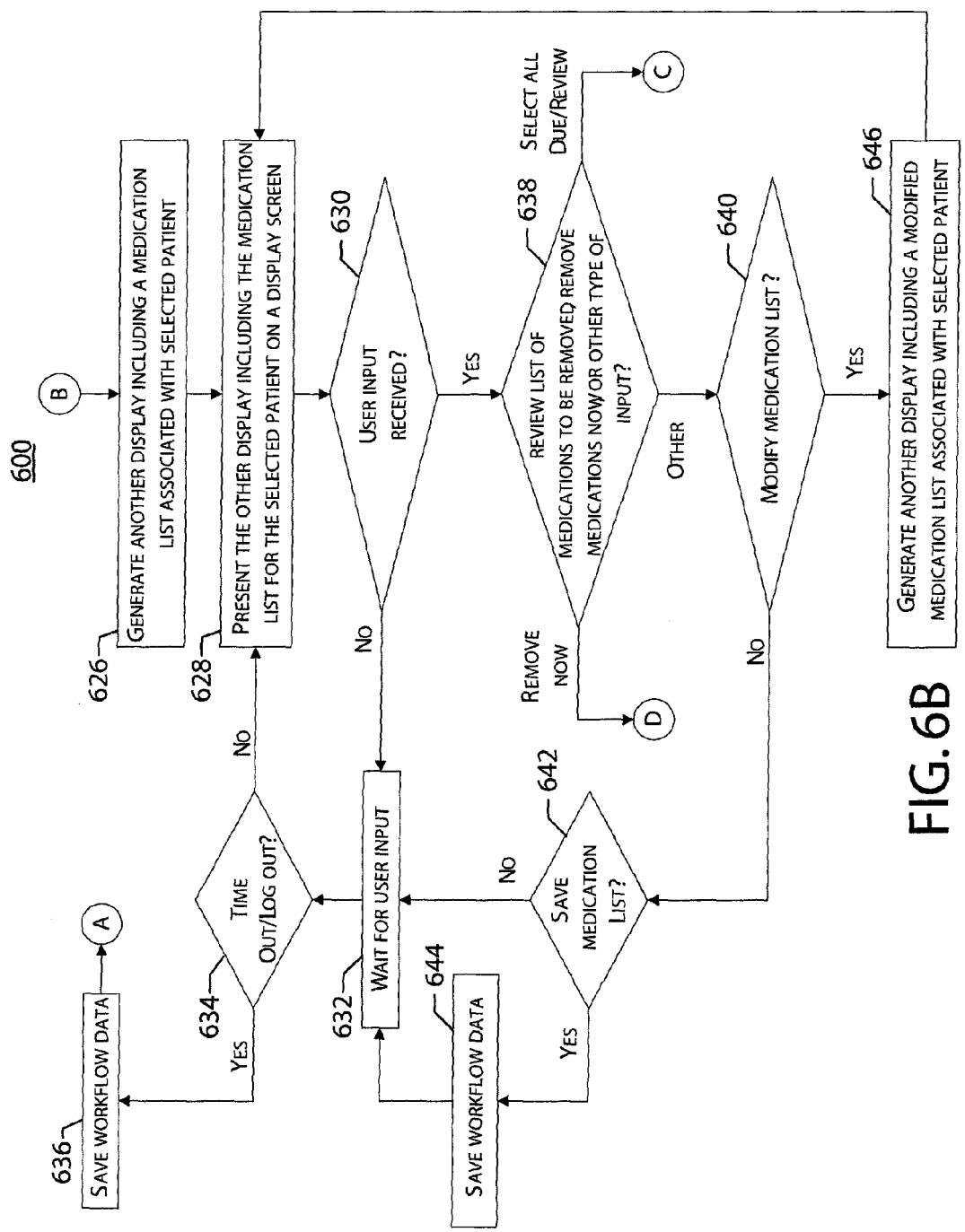
Figure 6C:
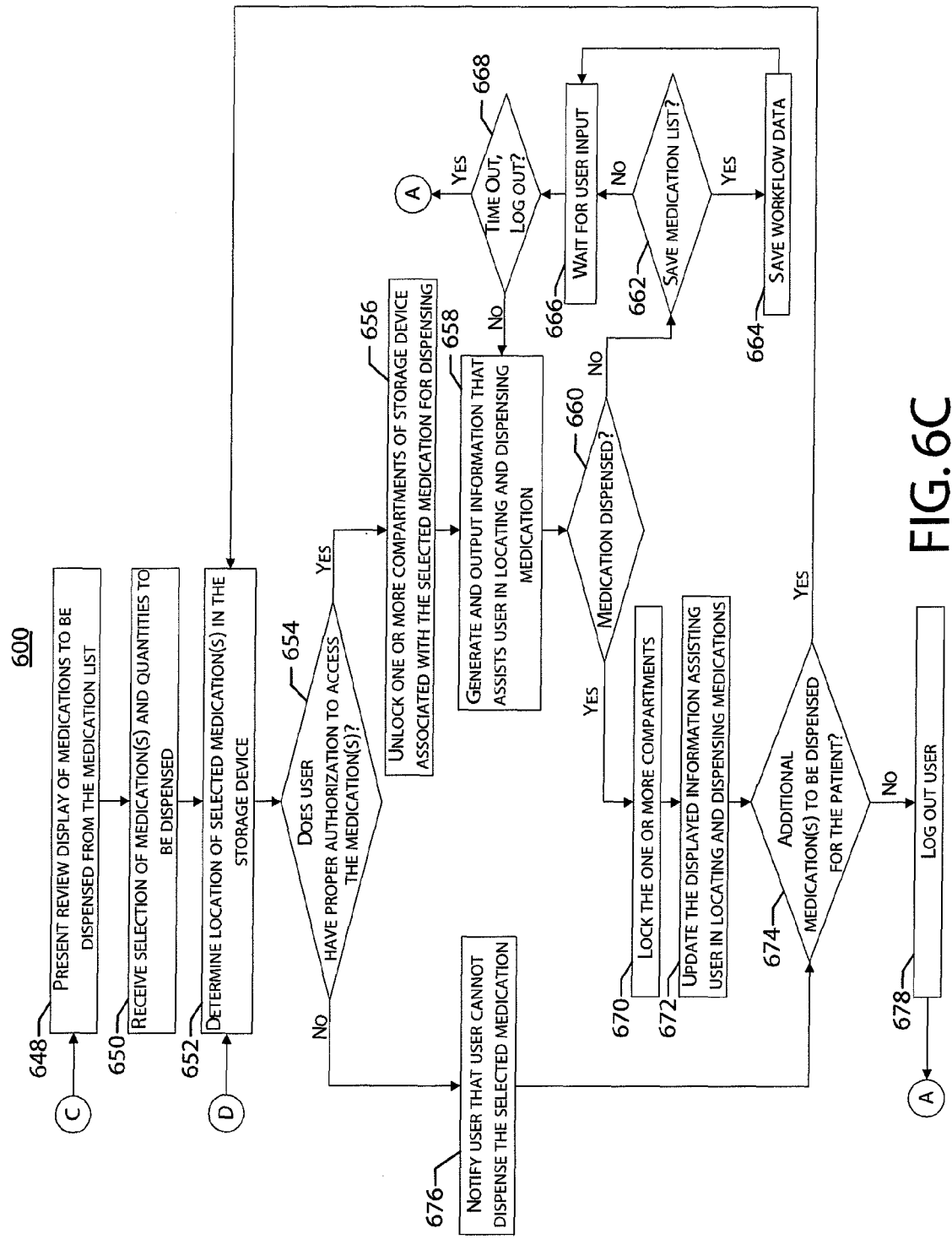

FIGS. 6A-6C shows process 600, which may be used in accordance with some embodiments to expedite the workflow and minimize or at least reduce the time required to dispense medication safely and securely from a storage device, such as storage device 5 discussed herein. Like some other processes discussed herein, process 600 is represented by a flow diagram in accordance with some exemplary methods, computer program products and/or systems discussed herein. It will be understood that each operation, action, step and/or other types of functions shown in the diagrams, and/or combinations of functions in the diagrams, can be implemented by various means. Means for implementing the functions of the flow diagrams, combinations of the actions in the diagrams, and/or other functionality of example embodiments of the present invention described herein, may include hardware and/or a computer program product including a computer-readable storage medium (as opposed to or in addition to a computer-readable transmission medium) having one or more computer program code instructions, program instructions, or executable computer-readable program code instructions stored therein. For example, program code instructions associated with FIGS. 6A-7 may be stored on one or more storage devices, such as memory 525, and executed by one or more processors, such as processor 505. Additionally or alternatively, one or more of the program code instructions discussed herein may be stored and/or performed by distributed components, such as those that may be connected to storage device 5 via a network or other communications interface. As will be appreciated, any such program code instructions may be loaded onto computers, processors, other programmable apparatuses (e.g., storage device 5) or network thereof from one or more computer-readable storage mediums to produce a particular machine, such that the particular machine becomes a means for implementing the functions of the actions discussed in connection with, e.g., FIGS. 6A-7 and/or the other drawings discussed herein.

The program code instructions stored on the programmable apparatus may also be stored in a non-transitory computer-readable storage medium that can direct a computer, a processor (such as processor 505) and/or other programmable apparatus to function in a particular manner to thereby generate a particular article of manufacture. The article of manufacture becomes a means for implementing the functions of the actions discussed in connection with, e.g., FIGS. 6A-7. The program code instructions may be retrieved from a computer-readable storage medium and loaded into a computer, processor, or other programmable apparatus to configure the computer, processor, or other programmable apparatus to execute actions to be performed on or by the computer, processor, or other programmable apparatus. Retrieval, loading, and execution of the program code instructions may be performed sequentially such that one instruction is retrieved, loaded, and executed at a time. In some example embodiments, retrieval, loading and/or execution may be performed in parallel by one or more machines, such that multiple instructions are retrieved, loaded, and/or executed together. Execution of the program code instructions may produce a computer-implemented process such that the instructions executed by the computer, processor, other programmable apparatus, or network thereof provide actions for implementing the functions specified in the actions discussed in connection with, e.g., process 600 of FIGS. 6A-6C.

Process 600 starts at 602 and proceeds to 604 where a user login screen is displayed. Like other displays discussed herein, a processor (such as the processor 505) and/or an output module (such as the output module 515) can generate a display and utilize a display device (such as the display device 30 and its circuitry) to present the display to the user (e.g., the user 45). The user login screen can prompt the user for various identifying information, including a user name, password, barcode, radio frequency identification ("RFID") access card, among other things. The storage device may obtain this information from, e.g., the various input components coupled thereto. Additionally, although many examples discussed herein refer to the storage device's and/or its processor's configuration, one or more other system components, such as a remotely located network device and/or remote storage device, may be configured to provide, used to provide and/or otherwise enable some of the functionality discussed herein.

At 606, the processor receives data associated with user identifying information from one or more user input components (e.g., via the input module 510). At 608, a determination is made by the processor as to whether or not the user has provided valid authorization credentials. In response to determining the user's credentials are not valid, process 600 proceeds to 610 and provides the user a notification that access will not be granted. The login screen may then be displayed again at 604 and the user may try to login again. In some embodiments, the process may end after a number of failed attempts and the processor may be configured to lock the storage device until an administrator or other predetermined user or type of user unlocks the storage device.

In response to determining at 608 that the user is authorized to access the storage device, process 600 proceeds to 612 and determines whether there is a saved workflow associated with the user. As discussed below, the storage device can be configured to save any changes the user and/or system make while selecting medications for dispensing. The storage device may also automatically save the user's progress after a predetermined period of time. Like other automatic functionality discussed here, the storage device may be configured to allow the user and/or system administrator to configure the automatic save functionality (e.g., ON/OFF, time period between automatic saves, etc.). The storage device may also be configured to save the user's progress upon determining a predetermined period of inactivity has elapsed (e.g., the system has "timed out"). In this regard, the user may choose to exit the workflow of process 600 (and/or any other workflow or variation thereof executed in accordance with embodiments discussed herein) or the user may have an emergency that causes the user to leave the storage device without logging out, and the storage device may be configured to save the user's progress for later access. Hence, the determination as to whether a previous workflow has been saved for any reason (e.g., automatically and/or manually) can be made at 612 and/or throughout process 600.

In response to determining at 612 that there is a saved workflow, the processor may be configured to retrieve, at 614, data associated with the last display and/or any modifications the user may have made regarding a patient list and/or configuration of displays. In this regard, the user may be able to resume work where the user left off before logging out of the system and/or the system automatically logging out the user.

In some embodiments, like other steps and functions discussed herein, the functions performed at 612 and 614 and/or similar functions to those performed at 612 and 614 may be repeated and/or otherwise performed at various points in process 600. For example, if the determination at 612 is made after selecting a patient at 620, the selected patient's medication list as modified and saved previously by the user may be generated and presented at 626 and 628, respectively. In this regard, an introductory screen may be presented (such as a patient listings display discussed below) and the changes made by the user may not be displayed until the user enters a submenu (such as a medication listing display discussed below).

A display including a list of patients may then be generated at 616 based on the data retrieved at 614. In some embodiments, rather than proceeding to 616, process 600 may be configured to proceed to another step, such as 628, if, for example, the storage device determines the workflow was last saved when the user was working on a particular patient. In some embodiments, a list of saved workflows may be generated by the processor and presented to the user, thereby enabling the user to select where process 600 proceeds after 614.

In response to determining at 612 that there are no saved workflows associated with the user's login credentials, the storage device may be configured to generate (at 616) and display (at 618) an initial display that includes a list of patients. An example of such a display is shown in FIG. 8.

Figure 8:
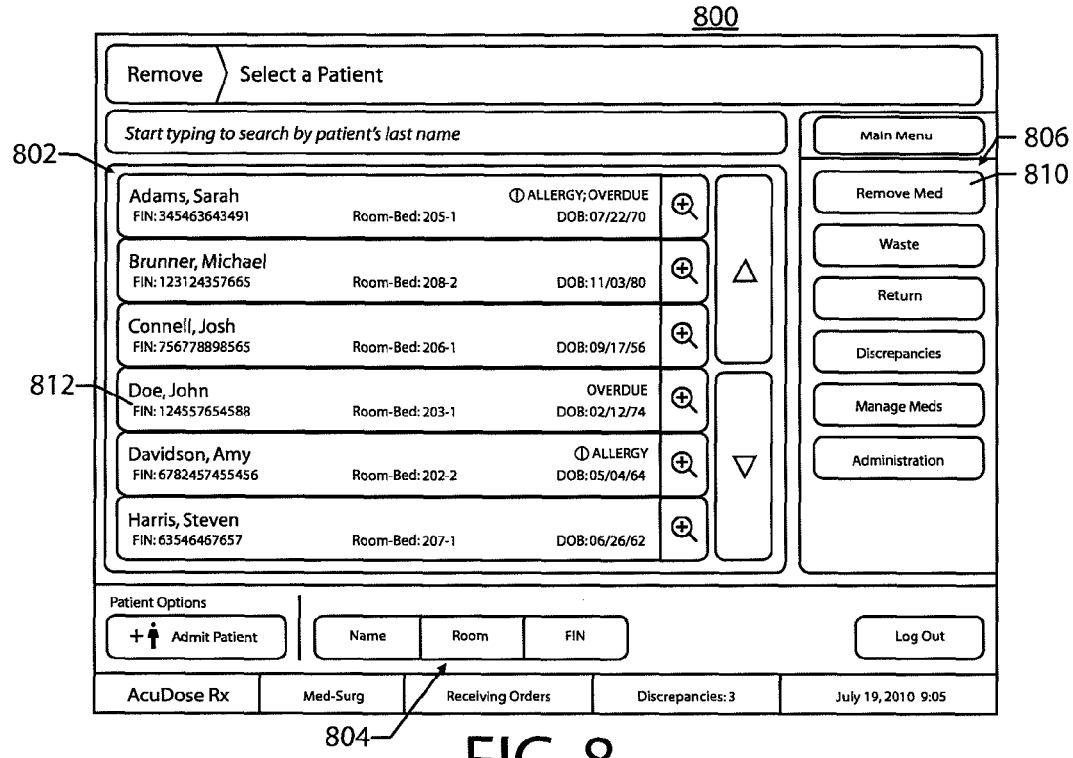

FIG. 8 shows patient listing display 800 that may be presented by, for example, a storage device's touch-sensitive display device. Among other things, patient listing display 800 may include patient listings 802, sorting option buttons 804, and listing modification buttons 806. Sorting option buttons 804 can be used to arrange the listings included in patient listings 802 in any number of ways, including alphabetically, by room number and/or by identification number (e.g., "FIN"). Listing modification buttons 806 can be used to modify and/or filter the listings included in patient listings 802. If a button is not enabled, it may be deselected as shown by remove med button 810 being darkened compared to the other buttons. The remove med button 810 can be darkened in any display, including patient listing display 800, that does not include any medications to be removed. Each listing, such as listing 812, may include various information about the selected patient, associated medication(s), and/or anything else. For example, each listing may include the patient's name, identification number, warning information (e.g., allergy information), date of birth information, hospital room-bed location assignment, current medical and/or medication status, potential discrepancies in the patient's other information, and/or any other information. One or more of the displayed pieces of information, as well as non-displayed pieces of information, may be used to sort the listings included in patient listing display 800. Each patient's information may be presented as a selectable listing (e.g., 812) and/or associated with an icon or other button (e.g., graphical or mechanical) that may be selected by the user. In response to a patient listing being selected, such as listing 812, a display dedicated to the medications associated with the selected patient may be displayed.

Returning to FIG. 6A, a determination is made at 620 whether one of the patients has been selected from the patient list presented in the first display. In response to determining that no patient has been selected, process 600 proceeds to 622 and waits for a user input indicating a desire to select a patient to begin the scheduling and/or dispensing of medication.

At 624, a determination is made by the processor whether a predetermined period of time has elapsed (e.g., since the user's last interaction with storage device 5) or if the user has decided to log out before selecting a patient from the list. If not, process 600 returns to 618. If the predetermined period of time has elapsed or if the user has decided to log out, process 600 returns to 604. In this regard, the storage device will not remain open for anybody to remove medication if the user gets distracted after logging into the system.

In response to determining that a patient has been selected from the patient list included in the patient list display, process 600 proceeds to 626 in FIG. 6B. Another display is generated (at 626) and displayed (at 628), which includes a medication list associated with the selected patient. An example of the medication list display associated with a patient is shown in FIG. 9.

Figure 9:
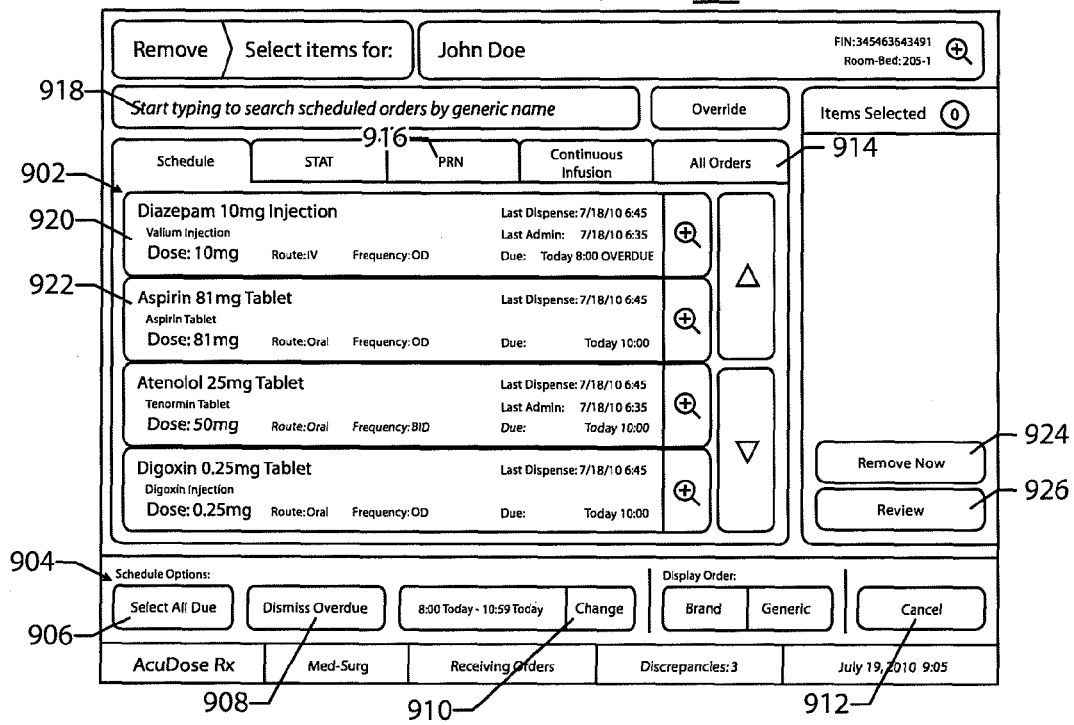

FIG. 9 shows medication listings display 900 that may be presented, for example, in response to listing 812 of FIG. 8 being selected. Among other things, patient listing display 900 may include medication listings 902 and schedule options 904, among other things. The medication listings display 900 can be generated at 626 based on data stored locally in the storage device (e.g., the memory 525) and/or downloaded from a remote storage device (such as a networked storage device). In some embodiments, the medication listings display may include the entire list of medications associated with a patient. When the entire list of medications is presented, additional information (such as when one or more of the medications are due, the time each medication was last administered to the patient, the medication's potential conflicts, known allergies of the patient, name brand/generic options, dosage information, potential conflicts between medications, authorization for current user to distribute particular medications, among other things) may also be presented in the medication listings 902.

In some embodiments, one or more additional buttons may be included in medication listings display 900 presented at 628. Process 600 may include decision steps for each of the buttons that are active to monitor for selection of the buttons. The buttons presented may be generated at 626 based on metadata associated with the user, metadata associated one or more of the medications, metadata identifying the date/time, metadata associated with the storage device, metadata associated with network(s) to which the storage device communicates, and/or anything else. The metadata may take any form, including bits of data, bytes of data, flags, etc., and be formatted in any suitable manner. The storage device (and/or any other machine) may use some or all the metadata to perform one or more pre-filtering processes that control which medication listings are included in the display (e.g., display 900 of FIG. 9) presented at 628 and/or eventually dispensed by the storage device. In this regard, the display presented at 628 may be pre-filtered by the system to only include medications due at a particular time of day (and/or window of time) and/or medications that are needed given the patient's current condition, among other things. Additionally or alternatively, schedule options 904 may be used by the user to generate user inputs indicative of how the user would like the listings to be (further) filtered and/or medications dispensed. For example, schedule options 904 may include select all due button 906, dismiss overdue button 908, and time window buttons 910.

At 630, the storage device may monitor for an indication of a user's selection. In response to not receiving a user input, process 600 may wait for a user input at 632.

After waiting a period of time, a determination can be made at 634 as to whether or not the user has decided to log out and/or whether the storage device should automatically log out the user. In response to determining at 634 the user should be logged out, process 600 proceeds to 636 and workflow data is saved. For example, the work flow data may include data associated with the selected patient so that the next time the user logs into the storage device (and/or another storage device networked thereto), the system is able to return the user to the display presented at 628 and/or give the user the option to return to the display presented at 628. In this manner, if the user gets distracted or interrupted while dispensing medication, the system can automatically lock itself without the user losing the work performed thus far (e.g., selected a patient).

In response to determining at 634 that the user should not be logged out, process 600 proceeds to 628 and continues to present the selected patient's medication listing display 900.

In response to determining that a user input was received at 630, a determination can be made at 638 as to whether, for example, there has been a selection of the select all due button 906, the remove now button 924, the review button 926, and/or any other button included in the display presented at 628 (e.g., display 900).

For example, in response to the all due button 906 being selected, the storage device can be configured to dispense only medications currently due (based on the current time of day). In some embodiments a new display, such as that shown in FIG. 10, may first be presented (at 648 of FIG. 6C) showing a "shopping cart" or other type of review display of only the medication listings associated with medications currently due. As such, the user is provided a one button solution (as opposed to adding each medication individually to a list and/or manually filtering by time) for dispensing all of the patient's medication for a given time window.

Additionally or alternatively, after determining at 638 that the review button 926 was selected, process 600 may advance to 648 and a review display may be presented. The functionality of the review button 926 and the select all due button 906 may appear similar to the user in that a review display is presented, such as that shown in FIG. 10 discussed below. But, in some embodiments, additional backend, automatic filtering may be executed in response to the select all due button 906 being selected (such as filtering based on time of day) that is not performed in response to the review button 906 being selected.

As yet another example, the example review display shown in FIG. 10 (and/or some steps of process 600) may be omitted in response to a determination at 638 that the remove now button 924 was selected. Instead, process 600 may proceed to 652, which is also discussed below.

As another example, at 640 the system can be configured to determine whether the user's input was indicative of a user's desire to modify the selected patient's medication list. In response to determining the other type user input received at 638 was not indicative of a user's desire to modify the medication list (such as cancel button 912 being selected, which may cause the storage device to move up the menu hierarchy to, e.g., the patient listing display 800), process 600 proceeds to 642 and determines whether the user would like to save the progress thus far.

In response to determining at 642 that the user would like to save the progress thus far, process 600 saves workflow data reflective of the medication list at 644. Process 600 then proceeds to 632. Process 600 may also proceed to 632 after determining the other user input was not to save the medication list and/or other data related to the user's interactions with the system thus far.

One or more other determining steps may be included additionally or alternatively in process 600 before proceeding to 632 to determine what the other user input may have been (including determining steps related to moving backwards in process 600, canceling the workflow of process 600, undoing a previous action/modification, among other things), but not all possible determining steps are shown nor discussed to avoid unnecessarily overcomplicating the disclosure.

In response to determining at 640 that a user input has been received indicative of the user's desire to modify the medication list, process 600 proceeds to 646 and modifies the medication list as the user desires. For example, selection of the dismiss overdue button 908, shown in FIG. 9, may cause the storage device to remove from the medication listings 902 all medications that were due in the past. In other words, after dismiss overdue button 908 is selected, only medications that are due during a given time window in the future may be left in medication listings 902. The given time window can be determined by the current time and/or by the user interacting with time window buttons 910 shown in FIG. 9. In some situations, the user may want to choose a future time window to queue the medications for dispensing later. The queue may be saved, as noted above. This feature allows the user to plan for dispensing ahead of time when the storage device is not being used or before a known busy time at the storage device (such as at the beginning of workers' shifts). For example, before leaving for the day, a user may log in and select the medications for dispensing the next morning and save his/her workflow before actually dispensing the medications. The next morning, instead of having to put together orders for each patient, the user may be able to log into the system, select a patient, and the storage device will provide the medication list that the user prepared the night before. In this regard, the user may begin the day by dispensing medications and skip all of the steps associated with selecting/modifying which medicines are to be dispensed for a particular patient.

Figure 7:
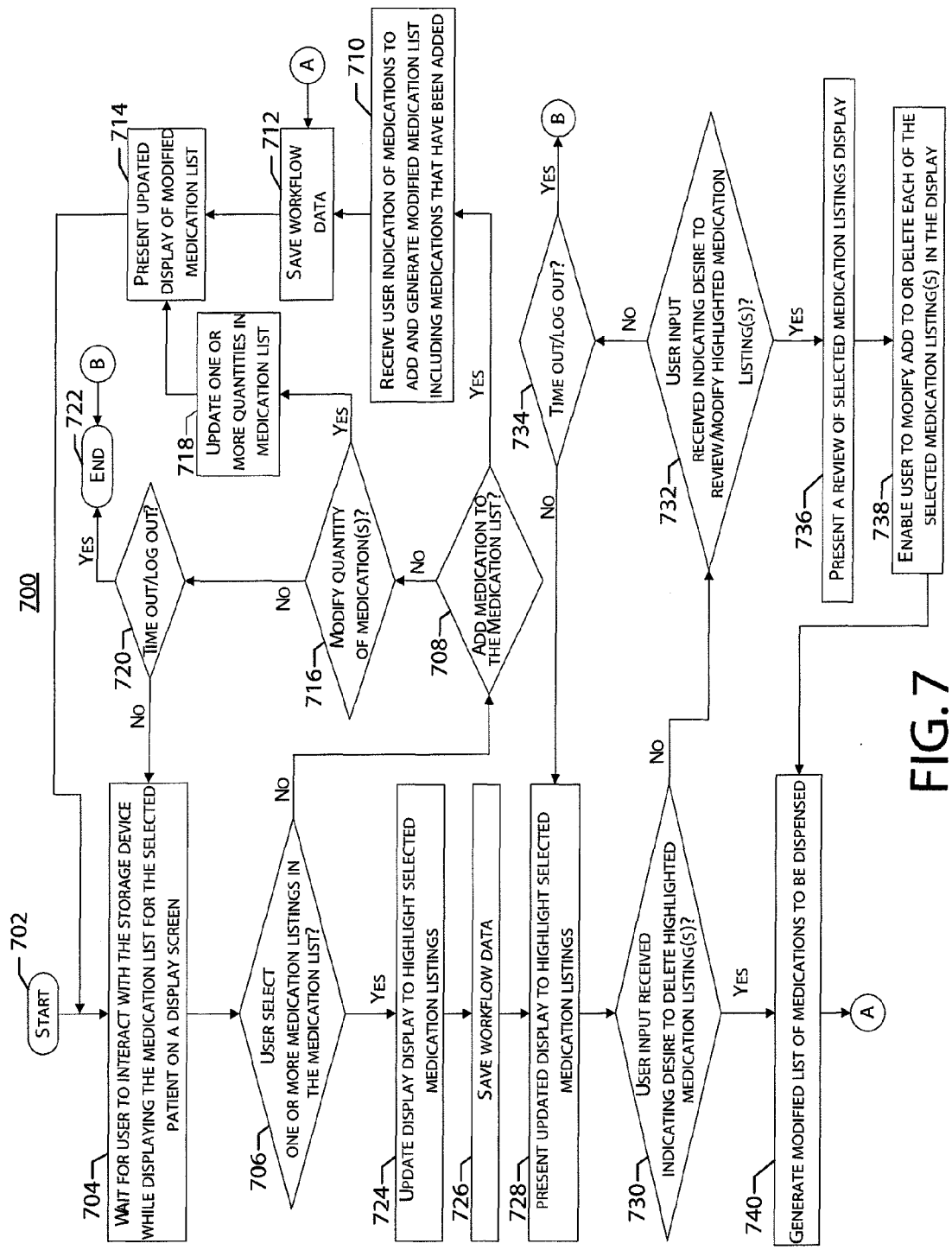

An exemplary sub-process, process 700, that gives further details associated with the modifying of a medication listing display at 640, is discussed in connection with FIG. 7. After modifying the medication list associated with the selected patient, process 600 may return to 628 and present a display including the modified medication listings display.

In response to determining at 638 that a review display is to be presented, which shows the medications to be dispensed, process 600 proceeds to 648 of FIG. 6C. For example, at 648, the processor can be configured to generate and present display 1000 shown in FIG. 10.

Display 1000 is illustrated as a shopping cart-type display that includes dispensing queue listings 1002. A dosage quantity, shown in dosage box 1004, can be associated with each queue listing and indicate the quantity of the associated medication that is to be removed. In some embodiments, the quantity in dosage box 1004 may need to be set by a user. In other embodiments, the quantity in dosage box 1004 can be pre-populated by the processor (based on, e.g., information entered by another user, such as a pharmacist) to show how many dosages per medication are to be dispensed. The user may have the ability to change the quantity to be removed using display 1000 by touching the "−" or "+" buttons flanking the numeric value included in dosage box 1004. In some embodiments, which are discussed in greater detail below, the number in dosage box 1004 may decrement automatically (at 658) as the user removes medication from the storage device. In other embodiments, a different display may include a count that is automatically decremented and/or manually decremented during the dispensing process (at 658).

Medication identifying box 1006 provides information about each medication that may be of interest and/or value to the user. Delete button 1008 can be used to remove the medication from the dispensing process. Selections of the medications and quantities to be dispensed as a result of user interactions with a review display, such as display 1000, can be received at 650.

In some embodiments, a user may select pick button 1010 of display 1000 and, in response a selection of a medication to be removed from the storage device is made at 652. The medication selected for removal can be based on medication(s) included in the display presented at 648 and/or modified at 650. In some embodiments, the selection can be based on medications(s) included in the display presented at 628 (such as in response to determining at 638 the remove now button 924 of FIG. 9 was selected). A determination can also be made at 652 as to the location of the medication selected for removal from the storage device. For example, the storage device can determine the pocket and/or drawer in which the medication is stored.

Next, at 654, process 600 can confirm that the user has the proper authorization to access the mediation selected for removal. For example, some medicines may only be administered by an anesthesiologist and/or other type of user that is certified by the employer and/or governing body to administer and/or handle the medication.

In response to determining at 654 that the user does have the proper authorization to access the medication, the storage device can be configured to unlock, at 656, the one or more compartments where the medication is stored. For example, the storage device can unlock the drawer(s) and/or lids of pockets where the selected medication is located.

At 658, the storage device can generate and output information that may assist the user in locating and dispensing the medication. Such information may help the user remember what is the next medication to be dispensed when a long list of medications is being dispensed and in the event something temporarily distracts the user while dispensing medications.

Displays 1100 and 1102 of FIGS. 11A and 11B, respectively are a first example of displays that may be generated and outputted to assist the user in locating and dispensing medications. Each of FIGS. 11A and 11B show displays particular to one drawer, pocket, other type of medication storage compartment and/or medication being dispensed. Because displays 1100 and 1102 can be dedicated to a medication storage compartment, the process can be expedited as compared to other processes. For example, if six medications are to be dispensed from two drawers of a storage device, display 1100 may be dedicated to dispensing the medications from the first drawer and display 1102 may be dedicated to dispensing medications from the second drawer. In this regard, each medication need not have its own display presented, thereby expediting the dispensing process by reducing the number of interactions the user may have with the storage device.

Each of FIGS. 11A and 11B are illustrated as comprising review panel 1104 that includes the list of medications being dispensed. As medication is removed from the storage device (as detected by, e.g., a sensor included in the storage device, a user input component scanning the medication, and/or by any other suitable means), the list in review panel 1104 can be updated dynamically (e.g., by deleting the removed medication, and/or by indicating its removal with a check mark, arrow, and/or other indication(s)) to show the medication next for dispensing and/or those that have already been dispensed. The information included in the review panel 1104 may be built as the medication list is built and may be presented in one or more additional screens, such as those shown in FIGS. 15A and 15B in preview panel 1506, while being built.

Figures 12, 13:

Display 1200 of FIG. 12 is another example of output information that may be generated and presented at 658. Display 1200 shows an example on-screen drawer layout that may help a user quickly find medications in a drawer of the storage device.

Furthermore, displays 1100, 1102 and 1200 may also allow the user to change the dosage quantity being dispensed and/or the count in a pocket on the screen. Displays 1100 and 1102 may each be more focused on a single medication being dispensed, while display 1200 may be more specific to a drawer being accessed and equally focused on all medications being dispensed from that drawer. Additionally or alternatively, lights in drawers (and/or elsewhere) and/or audio cues may be provided by the storage device to help the user quickly navigate to the medication being dispensed. In some embodiments, rather than present display 1100, 1102 and/or 1200, display 1000 of FIG. 10 may remain on the screen and be updated as medications are removed. For example, after a medication is removed, dosage box 1004 may be decremented as shown in FIG. 13. Although not shown, a preview and/or review panel (similar to review panel 1104 and/or preview panel 1506) may be included in display 1000 (and/or any other display).

In response to determining at 660 that the medication has not been fully dispensed (e.g., after a predetermined period of time), process 600 proceeds to 662 and determines if the medication list should be saved. In response to determining that the medication list should be saved, workflow data capturing the current state of the dispensing process may be generated and saved at 664 so that the user can resume the dispensing process more from this point (or after by-passing at least one of the previous steps) at a later time.

After 664 or in response to determining that the medication list should not be saved at 662, process 600 proceeds to 666 and waits for a user input. At 668 a determination is made as to whether the process should time out and/or the storage device should log out the user. In response to determining the process should log out the user, process 600 returns to 604 of FIG. 6A and presents a login screen. In response to determining that process 600 should continue without logging out the user, process 600 returns to 658.

In response to determining at 660 that the first selected medication has been fully dispensed (e.g., by sensors configured to monitor the removal of medication and/or the user's interactions with the storage device, including user interactions with the display screen), process 600 proceeds to 670 and locks the one or more compartments that were unlocked at 656. At 672, the information outputted at 658 may be updated. For example, display 1100 of FIG. 11B may be presented instead of display 1102 of FIG. 11A. As another example, FIG. 13 may be presented, which shows the dosage quantity in dosage box 1004 decremented from what was shown in FIG. 10. Once all the dosages for a particular medication are dispensed, the medication's listing may be removed from the list included in FIGS. 10 and 13. Additionally or alternatively, displays 1100 and 1102 may be replaced with another medication's display and/or display 1200 may be updated to remove the location of medications that have already been dispensed (leaving only those that need to be dispensed). Additionally or alternatively, workflow data may be saved at any point and/or any other information may be presented to the user, such as information confirming the dispensing of medication.

At 674 a determination is made as to whether additional medications should be dispensed for the patient based on the selected patient's medication list generated earlier in process 600. The determination at 674 may also follow a notification that the user cannot dispense the selected medication presented at 676 if it is determined that the user does not have the proper authorization to access the medication at 654.

In response to determining at 674 that more medications are to be dispensed, process 600 returns to 652. In response to determining at 674 that no more medications are to be dispensed for the selected patient, process 600 proceeds to 678 and logs the user out. Process 600 then returns to 604 and displays the user login screen.

An example process, process 700, for modifying the medication list at 640 is discussed in connection with FIG. 7. Process 700 starts at 702.

At 704, the processor can wait for the user to interact with the storage device while the storage device displays the medication list for the selected patient on the storage device's display screen. At 706, a determination can be made as to whether or not a user input has been received indicative of a selection of one or more medication listings currently displayed in the medication list.

In response to determining at 706 that there has been no user selection, a determination can be made at 708 as to whether or not there has been a user input indicative of a user's desire to add a medication to the medication list. For example, in some embodiments, the medication list may be pre-filtered automatically by the storage device to prevent certain medications from being displayed in the selected patient's medication list, and the user may wish to add or at least see options of medications that may be added to the medication list.

Figures 14A, 14B:

In response to the processor determining (e.g., from signals received from an input component) that a user input has been received indicative of a user's desire to add one or more medications to the list of medications to be dispensed for a patient, process 700 can proceed to 710 and receive a user indication of which medications to add. The indication of what medications to add may come from one or more user interactions with one or more display screens presented by the storage device. For example, in embodiments when the list of medications is pre-filtered, between 708 and 710, the storage device may be configured to present one or more lists of medications that had been filtered out due to, e.g., time of day, allergies, potential side effects, and/or any other metadata (some additional examples of which are provided above). For example, in response to selecting the select all orders button 914 and/or PRN tab 916 shown in FIG. 9, display 1400 of FIG. 14A or 1402 of FIG. 14B may be displayed. The checkmarks next to medications may indicate whether or not they were included in the pre-filtered list. Alternatively, display 1400 may be presented instead of display 900, and serve as a second example of the patient's medication listing display.

As another example, the storage device may also or instead allow a user to enter into field 918 (shown in FIG. 9) the name of one or more medications to be dispensed. In this regard, any method and/or system may be utilized to enable the user to add medications to the selected patient's medication list. A modified medication list may then be generated by the processor at 710, wherein the modified medication list includes the medications added by the user.

At 712, workflow data may be saved that enables the storage device to recall the modified medication list. In some embodiments, workflow data may be saved after each user interaction with the storage device and/or each user interaction associated with one or more particular steps of a process implemented by the storage device, such as step 710.

At 714, the modified medication list is presented to the user in a display, and process 700 returns to 704 at which point the modified medication list for the selected patient may continue to be displayed.

Returning to 708, if the user does not wish to add any medications to the list, a determination may be made at 716 as to whether or not a user input has been provided that is indicative of a desire to update one or more dosage quantities displayed in the medication list. In response to receiving an indication that at least one dosage quantity associated with a medication included the medication list is to be updated, the processor may update the list accordingly at 718. For example, the user may use a numeric keypad, arrow keys and/or soft buttons (presented on a touch display) to change the dosage quantity of one or more medications included in the medication list. In this regard, multiple medications' dosages may be modified by the user within the same screen presented by the storage device and during the same step of process 700. This is an improvement over, for example, using multiple screens to update dosages for multiple medicines, where each of the multiple screens allows only a single medication's dosage quantity to be changed. In this regard, the ability to change multiple medications' quantities in a single screen (such as that shown in FIGS. 10, 12 and 14) can help reduce the amount of time it takes to dispense multiple medications by a meaningful amount such as by almost to 45% (e.g., 2.45 minutes compared to 1.35 minutes). After updating the list with the new dosage information, process 700 proceeds to 718 and presents the updated display of the modified medication list. In some embodiments, as noted above, the user may also or instead be given the opportunity to update the dosage quantities associated with one or more medications while dispensing the medications.

In response to determining at 716 that all the dosage quantities associated with a medication included the medication list display are to remain the same (and/or in response to determining the storage device is not instructed by its processor to perform any other functions), process 700 may proceed to 720 and a determination may be made as to whether or not the user should be logged out. In response to determining the user should be logged out, process 700 ends at 722 (e.g., process 600 returns to 604 from 646, and a login screen can be displayed). In response to determining at 720 that the user should not be logged out, process 700 returns to 704.

In response to determining at 706 that there has been a user selection of one or more medication listings included in the medication list displayed at 704, the storage device can be configured to update the medication list display at 724, such that the selected medication listings are highlighted and/or otherwise distinguished (including being emphasized or deemphasized) as compared to the unselected medication listings. FIGS. 15A and 15B show examples of the medication listing display 1000 after listing 920 has been selected and after both listings 920 and 922 have been selected, respectively.

At 726, the workflow data can be saved automatically or manually (just as it can be saved at any time during process 700 as noted above for process 600). At 728, the updated display can be presented to the user with the selected medication listings, e.g., listings 920 and 922 of FIG. 15B, highlighted or otherwise distinguished from the unselected medication listings.

At 730, a determination can be made as to whether a user input was received indicative of the user's desire to delete the highlighted medication listing(s). For example, after selecting one or more listings, the user may touch or otherwise select a remove now button 1502. In response to determining at 730 that, for example, the remove now button 1502 was not selected, process 700 proceeds to 732.

At 732, a determination is made as to whether or not any user indication, including an indication to review or modify the selected medication listings, is received. For example, a determination is made whether review button 1504 is selected. If not, process 700 proceeds to 734 and determines if the user should be logged out. If so, process 700 returns to 722 and ends. If a determination is made the user need not be logged out, process 700 returns to 728 and the selected listings remain selected in a display, such as that shown in FIG. 15B, presented by the storage device.

In response to determining at 732 that an indication to review or modify the selected medication listings was received, the storage device may present the user a review display, such as that shown in FIG. 10, during which the user may review and/or modify information used to control the dispensing of medications. At 738, the user may be enabled by display 1000 shown in FIG. 10 to cause the storage device to modify, add to, delete and/or perform any other function in connection with the selected medication listings. For example, add medication button 1012 can enable the user to add a medication to the list.

After 738 or after determining at 730 that the user indicated a desire to delete the selected medication listings (e.g., to prevent the associated medications from being dispensed at this time), process 700 proceeds to 740 and the modified listing display is generated (e.g., with medication listings removed, changed, etc.). Process 700 may then return to 712 and the workflow can be saved.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of dispensing medication from a medication storage device, comprising:
   causing a patient list comprising a plurality of patients to be displayed by a display device;
   receiving a selection of a selected patient from the plurality of patients; and
   subsequent to receiving the selection:
   identifying a plurality of medications associated with the selected patient;
   determining a quantity associated with each of the medications;
   generating and causing to be displayed in a single user interface display, presented by the display device, a medication list comprising the medications and the quantity associated with each of the medications;

enabling a user to specify which of the medications of the medication list are to be dispensed and to modify the quantity associated with at least one of the medications by interacting with the single user interface display;

determining a storage location for each of the medications of the medication list that are to be dispensed;

providing for presentation of storage location information on the single user interface display wherein the storage location is presented illustrating the storage location on a graphical representation of at least a portion of a storage device, wherein the graphical representation of at least a portion of the storage device includes an indication of the quantity of medication to be dispensed at the location representative of the storage location of the medication to be dispensed;

determining if a user is authorized to access each of the medications of the medication list that are to be dispensed; and providing access to the storage location for each of the medications of the medication list that are to be dispensed in response to determining that the user is authorized to access each of the medications of the medication list that are to be dispensed.

2. The method of claim 1, wherein identifying the medications associated with the selected patient further comprises:
identifying the medications associated with the selected patient based at least in part on a time at which respective medications are scheduled to be administered to the selected patient.

3. The method of claim 1, wherein identifying the medications associated with the selected patient further comprises:
identifying the medications associated with the selected patient based at least in part on an identity of the user.

4. The method of claim 1, wherein the medications associated with the selected patient comprises all medications scheduled to be administered to the selected patient.

5. The method of claim 1, wherein enabling the user to specify which of the medications of the medication list are to be dispensed further comprises:
automatically selecting each medication of the medication list to be dispensed; and
enabling the user to deselect respective medications of the medication list.

6. The method of claim 1, wherein enabling the user to specify which of the medications of the medication list are to be dispensed further comprises:
enabling the user to select respective medications of the medication list.

7. The method of claim 1 further comprising:
receiving an instruction to dispense the medications; and
in response to receiving the instruction, generating and causing to be displayed a supplemental review display comprising a list of the medications and the quantity associated with each of the medications.

8. The method of claim 7, further comprising:
receiving an indication that one of the selected medications has been dispensed; and
in response:
updating the supplemental review display to remove the dispensed medication, or
updating the supplemental review display to otherwise indicate that the medication has been dispensed.

9. A storage device for dispensing medications, comprising:
one or more drawers configured to store a plurality of medications;
a display device; and
a processor configured to:
cause a patient list comprising a plurality of patients to be displayed by the display device;
receive a selection of a selected patient from the plurality of patients; and
subsequent to receiving the selection:
identify a plurality of medications associated with the selected patient;
determine a quantity associated with each of the medications;
generate and cause to be displayed in a single user interface display, presented by the display device, a medication list comprising the medications and the quantity associated with each of the medications;
enable a user to specify which of the medications of the medication list are to be dispensed and to modify the quantity associated with at least one of the medications by interacting with the single user interface display;
determine a storage location for each of the medications of the medication list that are to be dispensed;
provide for presentation of storage location information on the single user interface display wherein the storage location is presented illustrating the storage location on a graphical representation of at least a portion of the storage device, wherein the graphical representation of at least a portion of the storage device includes an indication of the quantity of medication to be dispensed at the location representative of the storage location of the medication to be dispensed;
determine if a user is authorized to access each of the medications of the medication list that are to be dispensed; and
provide access to the storage location for each of the medications of the medication list that are to be dispensed in response to determining that the user is authorized to access each of the medications of the medication list that are to be dispensed.

10. The storage device of claim 9, wherein the processor is further configured to identify the medications associated with the selected patient based at least in part on a time at which respective medications are scheduled to be administered to the selected patient.

11. The storage device of claim 9, wherein the processor is further configured to identify the medications associated with the selected patient based at least in part on an identity of the user.

12. The storage device of claim 9, wherein the medications associated with the selected patient comprises all medications scheduled to be administered to the selected patient.

13. The storage device of claim 9, wherein the processor is further configured to:
automatically select each medication of the medication list to be dispensed; and
enable the user to deselect respective medications of the medication list.

14. The storage device of claim 9, wherein the processor is further configured to enable the user to select respective medications of the medication list.

15. The storage device of claim 9, wherein the processor is further configured to:
receive an instruction to dispense the medications; and
in response to receiving the instruction, generate and cause to be displayed a supplemental review display comprising a list of the medications and the quantity associated with each of the medications.

16. The storage device of claim 15, wherein the processor is further configured to:
receive an indication that one of the selected medications has been dispensed; and
in response:
update the supplemental review display to remove the dispensed medication, or
update the supplemental review display to otherwise indicate that the medication has been dispensed.

17. A computer program product comprising at least one non-transitory computer-readable storage medium having computer-readable program code portions stored therein, the computer-readable program code portions comprising executable portions configured for:
causing a patient list comprising a plurality of patients to be displayed by a display device;
receiving a selection of a selected patient from the plurality of patients; and
subsequent to receiving the selection:
identifying a plurality of medications associated with the selected patient;
determining a quantity associated with each of the medications;
generating and causing to be displayed in a single user interface display, presented by the display device, a medication list comprising the medications and the quantity associated with each of the medications;
enabling a user to specify which of the medications of the medication list are to be dispensed and to modify the quantity associated with at least one of the medications by interacting with the single user interface display;
determining a storage location for each of the medications of the medication list that are to be dispensed;
providing for presentation of storage location information on the single user interface display wherein the storage location is presented illustrating the storage location on a graphical representation of at least a portion of a storage device, wherein the graphical representation of at least a portion of the storage device includes an indication of the quantity of medication to be dispensed at the location representative of the storage location of the medication to be dispensed;
determining if a user is authorized to access each of the medications of the medication list that are to be dispensed; and
providing access to the storage location for each of the medications of the medication list that are to be dispensed in response to determining that the user is authorized to access each of the medications of the medication list that are to be dispensed.

18. The computer program product of claim 17, wherein identifying the medications associated with the selected patient further comprises:
identifying the medications associated with the selected patient based at least in part on a time at which respective medications are scheduled to be administered to the selected patient.

19. The computer program product of claim 17, wherein identifying the medications associated with the selected patient further comprises:
identifying the medications associated with the selected patient based at least in part on an identity of the user.

20. The computer program product of claim 17, wherein the medications associated with the selected patient comprises all medications scheduled to be administered to the selected patient.

21. The computer program product of claim 17, wherein enabling the user to specify which of the medications of the medication list are to be dispensed further comprises:
automatically selecting each medication of the medication list to be dispensed; and
enabling the user to deselect respective medications of the medication list.

22. The computer program product of claim 17, wherein enabling the user to specify which of the medications of the medication list are to be dispensed further comprises:
enabling the user to select respective medications of the medication list.

23. The computer program product of claim 17 further comprising:
receiving an instruction to dispense the medications; and
in response to receiving the instruction, generating and causing to be displayed a supplemental review display comprising a list of the medications and the quantity associated with each of the medications.

24. The computer program product of claim 23 further comprising:
receiving an indication that one of the selected medications has been dispensed; and
in response:
updating the supplemental review display to remove the dispensed medication, or
updating the supplemental review display to otherwise indicate that the medication has been dispensed.

* * * * *